(12) United States Patent
Bamdad

(10) Patent No.: US 6,306,584 B1
(45) Date of Patent: Oct. 23, 2001

(54) ELECTRONIC-PROPERTY PROBING OF BIOLOGICAL MOLECULES AT SURFACES

(75) Inventor: Cynthia C. Bamdad, San Marino, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/843,623

(22) Filed: Apr. 10, 1997

Related U.S. Application Data

(63) Continuation-in-part of application No. 08/804,883, filed on Feb. 24, 1997, now abandoned, which is a continuation-in-part of application No. 08/786,153, filed on Jan. 21, 1997, now abandoned.

(51) Int. Cl.[7] .................................................. C12Q 1/68
(52) U.S. Cl. .............................. 435/6; 435/7.1; 536/24.3; 536/26.6
(58) Field of Search .................... 435/6, 7.6, 7.1, 435/7.7; 536/24.3, 26.6

(56) References Cited

U.S. PATENT DOCUMENTS

| | | | |
|---|---|---|---|
| 4,964,972 | 10/1990 | Sagiv et al. | 204/418 |
| 5,242,828 | 9/1993 | Bergström et al. | 435/291 |
| 5,436,161 | 7/1995 | Bergström et al. | 435/291 |
| 5,571,568 | * 11/1996 | Ribi et al. | 427/487 |
| 5,622,821 | * 4/1997 | Selvin et al. | 435/6 |

FOREIGN PATENT DOCUMENTS

| | | |
|---|---|---|
| 0515615 | 9/1996 | (DE) . |
| 0 589 867 | 5/1990 | (EP) . |
| 0 589 867 | 4/1996 | (EP) . |
| 6-41183 | 2/1994 | (JP) . |
| 90/05303 | 5/1990 | (WO) . |

* cited by examiner

*Primary Examiner*—Scott W. Houtteman
(74) *Attorney, Agent, or Firm*—Richard R. Trecartin; Robin M. Silva; Flehr Hohbach Test Albritton & Herbert LLP

(57) ABSTRACT

A technique for immobilizing biological molecules, in particular nucleic acid strands, is described. Biological molecules immobilized at surfaces can be used in electron-transfer detection techniques in which a binding partner of a biological molecule is brought into proximity of the surface-immobilized biological molecule, an electrical potential created between the two biologically-binding species, and electron transfer through the species determined. Another technique involves immobilizing a bioligical molecule such as a protein, DNA, etc. at a surface via a self-assembled monolayer, affecting the biological molecule via, for example, biological binding, inducing a change in conformation via a prion, etc., and detecting an electronic property change in the molecule via a change in inpedence associated with an electronic circuit addressed by the biological molecule. These technique facilitates combinatorial array detection articles.

12 Claims, 17 Drawing Sheets

ELECTRONIC-PROPERTY PROBING OF BIOLOGICAL MOLECULES AT SURFACES

RELATED APPLICATION

This application is a continuation-in-part of U.S. application Ser. No. 08/804,883 by Cynthia C. Bamdad entitled "Electronic-Property Probing of Biological Molecules at Surfaces", filed Feb. 24, 1997, now abandoned, which is a continuation-in part of U.S. application Ser. No. 08/786,153 by Cynthia C. Bamdad entitled "Surface-Immobilized Nucleic Acid and Electron-Transfer Devices and Methods Employing the Same", filed Jan. 21, 1997, now abandoned.

The United States Government has certain rights in this invention pursuant to grant number GM32308 from the National Institutes of Health.

FIELD OF THE INVENTION

The present invention relates generally to the derivatization of surfaces for determination of analytes, for example from a fluid medium using a biological binding partner of an analyte, and more particularly to the formation, on a surface, of a self-assembled molecular monolayer including a biological species such as a nucleic acid strand, and the use of the self-assembled monolayer in a probe that acts to detect molecular recognition via electronic properties of the biological species.

BACKGROUND OF THE INVENTION

Biochemical analyses are invaluable, routine tools in health-related fields such as immunology, pharmacology, gene therapy, and the like. In order to successfully implement therapeutic control of biological processes, it is imperative that an understanding of biological binding between various species is gained. Indeed, an understanding of biological binding between various species is important for many varied fields of science.

Many biochemical analytical methods involve immobilization of a biological binding partner of a biological molecule on a surface, exposure of the surface to a medium suspected of containing the molecule, and determination of the existence or extent of molecule coupling to the surface-immobilized binding partner.

The study of biological binding involving nucleic acid at surfaces has been hindered by the difficulty in immobilizing a single strand of nucleic acid at a surface without also immobilizing the complement of that strand. Where a single strand of nucleic acid is immobilized at a surface with its complement, it is not available for interaction by itself.

Electron transfer through model enzymes has been studied, and several theoretical models predict rates of transfer through these enzymes (Chidsey, C.E.D., "Free Energy and Temperature Dependence of Electron Transfer at the Metalelectrolyte Interface," *Science* 251 (1991), pp. 919–922). Comparison of predicted electron transfer rates with the time required for electrons to travel a finite distance within a protein has led to the conclusion that electrons traverse a pathway of chemical bonds such as covalent or hydrogen bonds (J. N. Onuchic, D. N. Beratan, J. R. Winkler, and H. B. Gray, *Ann. Rev. Biophys. Biomol. Struct.*, 21 349 (1992); D. N. Baratan, J. N. Onuchic, J. R. Winkler and H. B. Gray, *Science*, 258 1740 (1992); J. J. Regan, S. M. Risser, D. N. Beratan, and J. N. Onuchic, *J. Phys. Chem.*, 97 13083 (1993)), but do not travel through vacant space (S. M. Risser, D. N. Beratan, and T. J. Meade, *J. Am. Chem. Soc.*, 115 2508 (1993)). This finding was later modified to include electron transfer between π-stacked electron systems (F. Barigelletti, L. Flamnigni, V. Balzani, J. P. Collin, J. P. Sauvage, A. Sour, E. C. Constable, and A. C. M. W. Thompson, *J. Am. Chem. Soc.*, 116 7692 (1994); J. N. Onuchic and D. N. Beratan, *J. Am. Chem. Soc.*, 109 6771 (1987)). Subsequently, several groups measured rates of electron transfer through electroactive proteins (enzymes) using modified or unmodified electrodes, then microelectrodes (Hill, H. A. O., Klein, N. P., Murthy, A. S. N., Psalti, I. S. N., *Chemical Sensors and Instrumentation*, (1989) pp. 105–113; Armstrong, F. A., Bond, A. M., Hill, H. A. O., Psalti, I. S. N., Zoski, C. G., *J. Phys. Chem.* 93, (1989) pp. 6485–6493).

One drawback in these studies is that direct adsorption of protein onto an electrode typically resulted in loss of conductivity, presumably due to protein denaturation. A hydrophilic molecule (promoter) therefore was adsorbed to an electrode prior to adsorption of the electroactive protein in some cases. The promoter layer is designed to bind the protein of interest through hydrogen bonds, giving the electrons a suitable pathway. Notably, in these studies, electrons were observed to travel through an inert molecule, then through the electroactive molecule (Hill, H. A. O. and Lawrence, G. A., "Some Consequences of Mixed and Dilute Surface Modification of Gold Electrodes for Protein Electrochemistry," *J. Electroanal. Chem.* 270 (1989) pp. 309–318). The amplitude of the signal was dependent upon the potential difference.

Rates of electron transfer have also been measured through DNA (C. J. Murphy, M. R. Arkin, Y. Jenkins, N. D. Ghatlia, S. H. Bossman, N. J. Turro and J. K. Barton, *Science*, 262 1025 (1993)). It has been shown that the rate of electron transfer through double-stranded DNA is much faster than through single-stranded DNA (T. J. Meade and Jon F. Kayyem, *Angew. Chem. Int. Ed. Engl.*, 34 3, pp. 352–354 (1995), "Electron Transfer through DNA: Site-Specific Modification of Duplex DNA with Ruthenium Donors and Acceptors").

Co-pending, commonly-owned U.S. patent application Ser. No. 08/312,388, filed Sep. 26, 1994 by Bamdad, et al., describes a technique for immobilization of single-stranded DNA at a surface as part of a self-assembled monolayer, and use of the arrangement in determination of biological binding partners of the DNA via Surface Plasmon Resonance (SPR), a technique that measures the very slight changes in mass that occurs at a surface upon biological binding of a binding partner to the surface-immobilized species.

Accordingly, it is an object of the invention to provide techniques for studying molecular interactions at surfaces.

SUMMARY OF THE INVENTION

The foregoing and other objects and advantages of the invention are achieved by providing a molecule having a formula X—R—Ch, in which X represents a functional group that adheres to surface such as a gold surface, R represents a spacer moiety that promotes formation of a self-assembled monolayer of a plurality of the molecules, and Ch represents a bidentate, tridentate, or quadradentate chelating agent that coordinates a metal ion. The chelating agent includes a chelating moiety and a non-chelating linker moiety, such that it can be covalently linked via its linker moiety to the spacer moiety while allowing the chelating moiety to coordinate a metal ion. According to a preferred aspect of the invention a metal ion is coordinated to the chelating agent, and a binding partner of a target molecule is coordinated to the metal ion. This arrangement is facilitated by selecting the chelating agent in conjunction with the metal ion such that the chelating agent coordinates the metal ion without completely filling the ion's coordination sites, allowing the binding partner to coordinate the metal ion via coordination sites not filled by the chelating agent. According to one aspect of the invention the binding partner is a biological species that includes a polyamino acid tag, such as a tag made up of at least two histidine residues, that coordinates the metal ion. In this context the term "adhere" means to chemisorb in the manner in which, for example, alkyl thiols chemisorb to gold.

The present invention also provides a species having a formula X—R—Ch—M—BP—BMol, in which X represents a functional group that adheres to a surface, R represents self-assembled monolayer-promoting spacer moiety, Ch represents a chelating agent that coordinates a metal ion, M represents a metal ion coordinated by the chelating agent, BP represents a biological binding partner of a biological molecule, and BMol represents the biological molecule. The binding partner is coordinated to the metal ion.

The invention also provides an article including a solid phase that has a surface. A plurality of chelating agents are immobilized at the surface in such a way that essentially each of the chelating agents is oriented so as that the chelating moiety of the agent, that is the electron donating portions of the agent, face in a direction away from the surface and is unencumbered by species, such as other chelating agents, that would interfere with the chelating function. This can be accomplished by isolating the chelating agent at the surface by non-chelating species. In this way each chelating agent can coordinate a metal ion so as to expose in a direction away from the surface at least two free metal coordination sites. According to one aspect of the invention the article includes a surface and a self-assembled mixed monolayer adhered to the surface and formed of at least a first and a second species. The first species has a formula X—R—Ch, where X, R, and Ch are each selected such that X represents a finctional group that adheres to the surface, R represents a spacer moiety that promotes self-assembly of the mixed monolayer, and Ch represents a chelating agent that coordinates a metal ion. The second species is selected to form a mixed self-assembled monolayer with the first species, and the mixed monolayer is made up of at least 70 mol percent of the second species. The second species preferably is a species selected to inhibit non-specific binding of a protein to the surface.

According to a preferred aspect, the article is suitable for capturing a biological molecule. According to this aspect a self-assembled mixed monolayer, formed of a first species and a second species, is adhered to the surface. The first species has a formula X—R—Ch—M—BP, where X, R, Ch, M, and BP are each selected such that X represents a functional group that adheres to the surface, R represents a spacer moiety that promotes self-assembly of the mixed monolayer, Ch represents a chelating agent that coordinates a metal ion, M represents a metal ion, and BP represents a binding partner of the biological molecule. The binding partner is coordinated to the metal ion. The second species is selected to form a mixed, self-assembled monolayer with the first species, and according to a preferred aspect the second species has a formula, X—R—O—(CH$_2$CH$_2$—O)$_n$—H, in which X represents a functional group that adheres to the surface, R represents a spacer moiety that promotes formation of a self-assembled monolayer of a plurality of the molecules, and n is from one to ten. The article can be constructed and arranged to facilitate instrumental determination of an analyte, and according to a preferred aspect is a biosensor element such as a SPR chip.

The present invention also provides a method of making an article for capturing a target molecule. The method of making the article includes formulating a solution containing a mixture of at least a first and a second species, and exposing to the solution a surface of the article for a period of time sufficient to form a self-assembled mixed monolayer of the first and second species on the surface. The first species has a formula X—R—Ch as described above. The second species is selected to form a mixed self-assembled monolayer with the first species, and the second and first species are present in the solution at a molar ratio of at least 70:30.

The present invention also provides a method of capturing a biological molecule. The method involves contacting a medium suspected of containing the biological molecule with a solid phase that has a surface carrying a plurality of binding partners of the biological molecule, in which essentially all of the binding partners are oriented to expose away from the surface a recognition region for the biological molecule. The biological molecule then is allowed to biologically bind to the binding partner, and the biological molecule bound to the binding partner then can be determined. According to one aspect the method involves providing a solid phase having a surface, a chelating agent immobilized at the surface, a metal ion coordinated by the chelating agent, and a biological binding partner of the biological molecule coordinated to the metal ion. According to this aspect the surface is brought into contact with a medium suspected of containing the biological molecule for a period of time sufficient to allow the biological molecule to biologically bind to the binding partner.

The present invention provides another method of capturing a biological molecule. The method involves providing a solid phase having a surface, and a metal ion immobilized at the surface in such a way that the metal ion has at least two free coordination sites. A biological binding partner of a biological molecule is coordinated to the metal ion via a polyamino acid tag, and a medium containing the biological molecule is brought into contact with the surface, whereupon the biological molecule is allowed to biologically bind to the binding partner. The biological molecule then can be determined.

The present invention provides yet another method of capturing a biological molecule. This method involves providing a solid phase that has a surface having adhered thereto a species having a formula X—R—Ch—M—BP, in which X represents a functional group that adheres to the surface, R represents a self-assembled monolayer-promoting spacer moiety, Ch represents a chelating agent that coordinates a metal ion, M represents a metal ion coordinated by the chelating agent, and BP represents a binding partner of the biological molecule, coordinated to the metal ion. A target molecule then is allowed to biologically bind to the binding partner. The biological molecule then can be determined, for example by detecting a physical change associated with the surface.

An article provided in accordance with the invention can be a biosensor element, such as a SPR chip, and the determination carried out by measuring surface plasmon resonance associated with the chip. The methods of the invention that involve capturing a molecule can involve removal of a preselected molecule, such as a biological molecule, from a fluid medium.

The present invention also provides sensing elements fashioned as described above and suitable for use in a biosensor, for determination of a biological molecule and in particular a molecule that is a binding partner of a nucleic acid strand. A particularly preferred sensing element includes a substrate, a metal film having a surface, and a self-assembled monolayer of a species X—R—R—NA or X—R—NA—NAB. X represents a finctional group that adheres to the surface, R represents a spacer moiety that promotes formation of a self-assembled monolayer of a plurality of the species, NA represents a nucleic acid strand, and NAB represents a nucleic acid strand that is a binding partner of NA and a binding partner of the biological molecule to be determined.

The present invention also provides a kit including an article having a surface and a molecule X—R—Ch, both as described above. The kit can include M and BP, either separately or combined as species X—R—Ch—M or X—R—Ch—M—BP, where X, R, Ch, M, and BP are as described herein. The kit also can include X—R—NA, optionally with NAB, or X—R—NA—NAB as described herein.

Another aspect of the invention is the article formed when the foregoing molecule(s) is adhered to a surface, preferably gold. In this embodiment the article has a chelating agent as described above attached to a spacer moiety as described above which in turn is adhered via X.

In another aspect the invention provides a self-assembled monolayer including a species X—R—R—Ch as described above, wherein at least 90% of the Ch units are isolated from all other Ch units. In one embodiment, the Ch units are isolated from each other by at least 5 nm. They can be isolated from each other by a biologically-inert self-assembled monolayer-forming species.

In another aspect, the invention provides a self-assembled monolayer-forming species including a nucleic acid strand. The nucleic acid strand can be single-stranded DNA or double-stranded DNA, or another species. The nucleic acid strand can be a single nucleic acid strand free of hybridization from a complementary strand, and/or can form a part of a self-assembled monolayer of other nucleic acid strand species. The nucleic acid strand can be covalently coupled to a self-assembled monolayer-forming species, thereby forming a part of a self-assembled monolayer.

The invention also provides a single nucleic acid strand that is immobilized at a surface, which immobilization can be covalent immobilization, and the strand is not removable from the surface under disassociation conditions and is free of hybridization to any nucleic acid strand not removable from the surface under disassociation conditions. The nucleic acid strand, according to this aspect, can be hybridized to a complementary nucleic acid strand that is disassociable from the single strand under disassociation conditions.

According to another aspect, the invention provides a surface on which is a self-assembled A z monolayer including a plurality of self-assembled monolayer-forming species each including a nucleic acid strand. At least 90% of the nucleic acid strands are biologically isolated from all other a nucleic acid strands in this aspect. At least 90% of the nucleic acid strands are isolated from each other by at least 5 nm according to one embodiment, and can be isolated from each other by a biologically inert self-assembled monolayer-forming species.

According to another aspect, the invention provides a method including providing a single nucleic acid strand immobilized at a surface, and allowing a biological binding partner of the nucleic acid strand to biologically bind to the strand. The single nucleic acid strand can be covalently immobilized to the surface or immobilized in any other way as part of a self-assembled monolayer in preferred embodiments, and preferably is isolated from other single nucleic acid strands as described above. Alternatively, double-stranded nucleic acid can be immobilized at the surface in this way. In one embodiment, the biological binding partner is a nucleic acid strand that is complementary to the nucleic acid strand immobilized at the surface. In another embodiment the binding partner is a protein or the like.

According to another aspect the invention provides a method including introducing an electron into a first biological species. The first biological species is one of a pair of biological binding partners defined by the first biological species and a second biological species. The electron then is passed through the first species into the second species, and removed from the second species. The first and second species can be nucleic acid strands that are complimentary, and one or both can be immobilized at a surface of a respective article. When the respective articles are electrodes included in an electrical circuit, the method can involve determining electronic transfer through the biological species.

An array of biological species of this type can be provided on a surface. That is, biologically distinct species (species including binding properties distinct from each other; species that will not biologically bind to each other) can be immobilized on the surface, preferably via a self-assembled monolayer, preferably covalently, and preferably in a manner in which they are isolated from each other by at least 5 nanometers. These distinct biological species can be addressed by other biological species that might bind biologically to one or more of these species, and where binding occurs electrical current flows, and identification of a biological species is made.

In another aspect, the invention provides a method that involves passing an electron through a biological species linked to a self-assembled monolayer-forming species immobilized at a surface of an article.

In another aspect, the invention involves a method including providing a first biological species that is linked to a surface of a first article via a self-assembled monolayer. A second biological species also is linked to the same surface via a self-assembled monolayer. An electron is passed through the first biological species while the second biological species does not pass an electron. The electron passed through the first biological species can be passed from the article into the species, or from the species into the article.

According to another aspect the invention provides a method including providing a first biological species immobilized at a surface of a first article and a second biological species immobilized to the surface of the first article. An electron is passed through the first biological species while the second biological species does not pass an electron.

The invention also provides an article including a first electrode having a surface, a second electrode having a surface, and an electrical circuit connecting the first and second electrodes. A first biological species is immobilized at a surface of the first electrode, and a biological binding partner of the first biological species is immobilized at the second electrode.

In another aspect the invention provides a method involving determining the interaction of a first molecule with a second molecule by detecting a change in electronic configuration of the second molecule due to interaction of the second molecule with the first molecule. In one aspect the determining step involves exposing the second molecule to a medium suspected of containing the first molecule and determining the presence of the first molecule in the medium. The second molecule can be immobilized at a surface via a spacer moiety and the determining step can involve the first molecule to interact with the second molecule and determining a change in electronic configuration in the second molecule via detection involving electron transfer through the spacer moiety between the surface and the second molecule. The determining step can also involve determining a change in impedance of a system including the second molecule, after interaction with the first molecule, relative to an impedance measurement of the system without interaction with the first molecule.

The invention also provides a method involving immobilizing a protein at a surface, inducing a change in the conformation of the protein at the surface, and detecting the change in conformation.

The invention also provides a method involving providing a protein exposing the protein to a prion or associated cofactor, and determining a change in conformation of the protein induced by exposure of the protein to the prion.

Also provided is a method involving determining a disease state involving mis-folded protein in a physiological sample of a living mammal.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure.

DETAILED DESCRIPTION OF THE INVENTION

Figure 1:
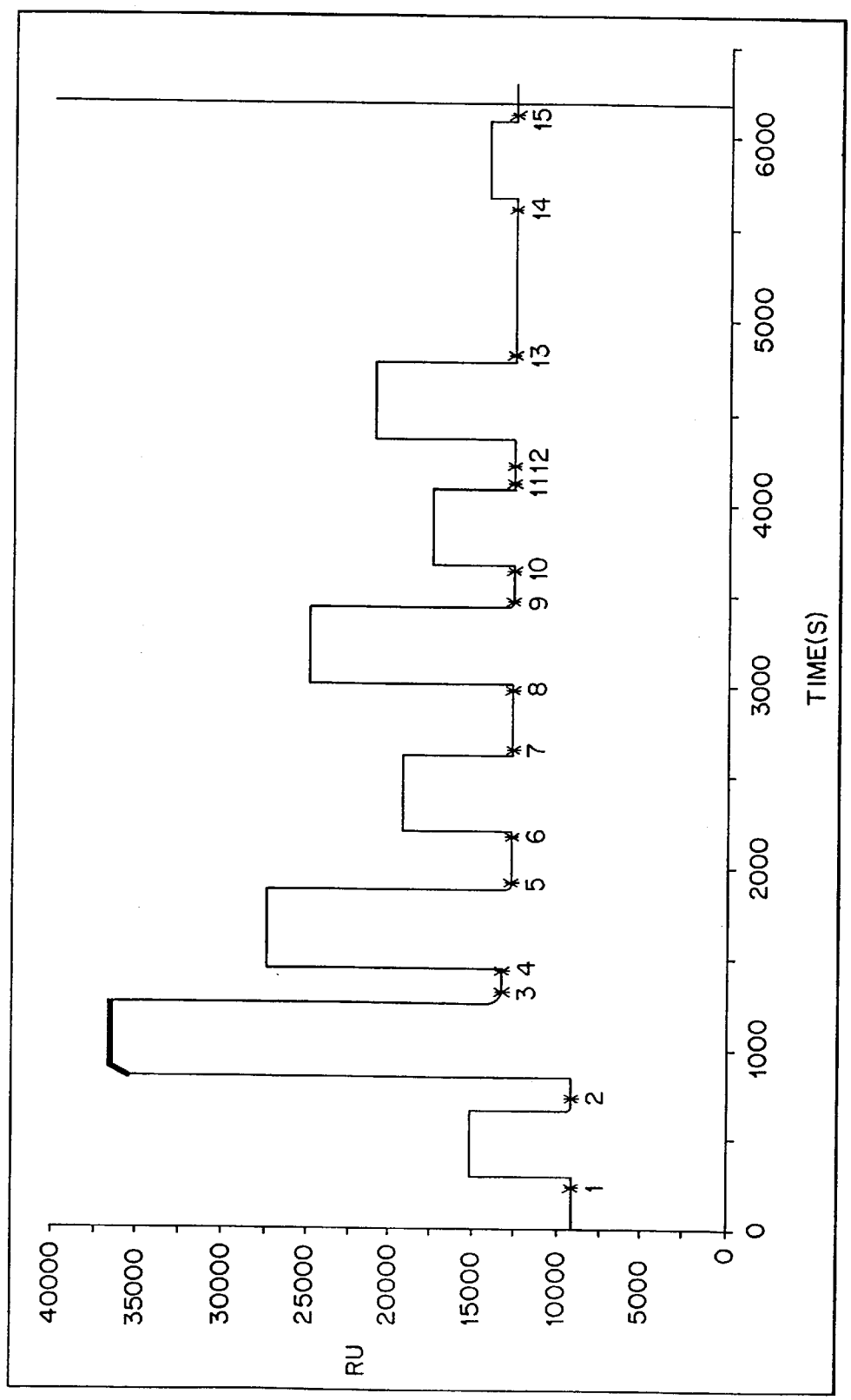
FIG. 1 is a SPR sensorgram illustrating response of a prior art chip carrying Gal 11 to SRB2.

Co-pending, commonly-owned application Ser. No. 08/312,388 entitled "Molecular Recognition at Surfaces Derivatized with Self-Assembled Monolayers" by Bamdad, et al., filed Sep. 26, 1994; co-pending, commonly-owned application Ser. No. 08/786,187 entitled "Molecular Recognition at Surfaces Derivatized with Self-Assembled Monolayers" by Bamdad, et al., filed Jan. 21, 1997, co-pending, commonly-owned application Ser. No. 08/786,153 entitled "Surface-Immobilized Nucleic Acid and Electron-Transfer Devices and Methods Employing the Same" by Bandad, et al., filed Jan. 21, 1997, and co-pending, commonly-owned application Ser. No. 08/616,929, filed Mar. 15, 1996 by Kim, et al., entitled "Method of Forming Articles and Patterning Surfaces via Capillary Micromolding"; U.S. application Ser. No. 08/131,838, filed Oct. 4, 1993, entitled "Method of Formation of Microstamped Patterns on Plates for Adhesion of Cells and Other Biological Materials, Devices and Uses Therefor", by Singhvi, et al.; and U.S. Pat. No. 5,512,131, issued Apr. 30, 1996 to Kumar, et al., all are incorporated herein by reference.

Nomenclature

The following definitions are provided to facilitate a clear understanding of the present invention.

The term, "chelating agent" refers to an organic molecule having unshared electron pairs available for donation to a metal ion. The metal ion is in this way coordinated by the chelating agent. Two or more neighboring amino acids can act as a chelating agent.

The terms, "bidentate chelating agent", "tridentate chelating agent", and "quadradentate chelating agent" refer to chelating agents having, respectively, two, three, and four electron pairs readily available for simultaneous donation to a metal ion coordinated by the chelating agent.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo biological binding with a particular biological molecule. For example, Protein A is a binding partner of the biological molecule IgG, and vice versa.

The term "biological molecule" refers to a molecule that can undergo biological binding with a particular biological binding partner.

The term "recognition region" refers to an area of a binding partner that recognizes a corresponding biological molecule and that facilitates biological binding with the molecule, and also refers to the corresponding region on the biological molecule. Recognition regions are typified by sequences of amino acids, molecular domains that promote van der Waals interactions, areas of corresponding molecules that interact physically as a molecular "lock and key", and the like.

The term "biologically inert", when describing the relationship between two species means that the two species do not undergo biological binding.

The term "coordination site" refers to a point on a metal ion that can accept an electron pair donated, for example, by a chelating agent.

The term "free coordination site" refers to a coordination site on a metal ion that is occupied by a water molecule or other species that is weakly donating relative to a polyamnino acid tag, such as a histidine tag.

The term "coordination number" refers to the number of coordination sites on a metal ion that are available for accepting an electron pair.

The term "coordinate bond" refers to an interaction between an electron pair donor and a coordination site on a metal ion leading to an attractive force between the electron pair donor and the metal ion.

The term "coordination" refers to an interaction in which one multi-electron pair donor, such as a chelating agent or a polyamino acid tag acting as a chelating agent, coordinatively bonds (is "coordinated") to one metal ion with a degree of stability great enough that an interaction that relies upon such coordination for detection can be determined by a biosensor. The metal ion is coordinated by the multi-electron pair donor.

The term "solid phase" refers to any material insoluble in a medium containing a target molecule or biological molecule that is desirably captured in accordance with the invention. This term can refer to a metal film, optionally provided on a substrate.

The term "surface" refers to the outermost accessible molecular domain of a solid phase.

The term "capturing" refers to the analysis, recovery, detection, or other qualitative or quantitative determination of an analyte in a particular medium. The medium is generally fluid, typically aqueous. The term, "captured", refers to a state of being removed from a medium onto a surface.

The term "target molecule" refers to a molecule, present in a medium, which is the object of attempted capture.

The term "determining" refers to quantitative or qualitative analysis of a species via, for example, spectroscopy, ellipsometry, piezoelectric measurement, immunoassay, and the like.

The term "immobilized", used with respect to a species, refers to a condition in which the species is attached to a surface with an attractive force stronger than attractive forces that are present in the intended environment of use of the surface and that act on the species, for example solvating and turbulent forces. Coordinate and covalent bonds are representative of attractive forces stronger than typical environmental forces. For example, a chelating agent immobilized at a surface, the surface being used to capture a biological molecule from a fluid medium, is attracted to the surface with a force stronger than forces acting on the chelating agent in the fluid medium, for example solvating and turbulent forces.

The term "non-specific binding" (NSB) refers to interaction between any species, present in a medium from which a target or biological molecule is desirably captured, and a binding partner or other species immobilized at a surface, other than desired biological binding between the biological molecule and the binding partner.

The tern "self-assembled monolayer" refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis, P. E.; Hickman, J.; Wrighton, M. S.; Whitesides, G. M. *Science* 245, 845 (1989), Bain, C.; Evall, J.; Whitesides, G. M. *J. Am. Chem. Soc.* 111, 7155–7164 (1989), Bain, C.; Whitesides, G. M. *J. Am. Chem. Soc.* 111, 7164–7175 (1989), each of which is incorporated herein by reference.

The term "self-assembled mixed monolayer" refers to a heterogeneous self-assembled monolayer, that is, one made up of a relatively ordered assembly of at least two different molecules.

The present invention provides a technique for molecular recognition at surfaces that involves electron transfer through a biological species immobilized at the surface. The surface presenting the immobilized biological species is exposed to a biological binding partner of the biological species, or a biological binding partner of a biological binding partner of the species, and electron transfer through the biological species and the biological binding partner determined.

In the case of many biological molecules, biological binding is extremely sensitive to orientation and conformation of the members involved in the binding, that is, the biological molecule and the binding partner. Accordingly, the manner of presentation of the binding partner at the surface to a medium containing the biological molecule is directly related to the sensitivity, and success, of the technique. The present invention presents a biological species such as a nucleic acid stand at the surface in a manner in which biological binding with the nucleic acid strand at the surface is facilitated (as described in the co-pending, commonly-owned applications both entitled "Molecular Recognition at Surfaces Derivatized with Self-Assembled Monolayers", one filed Sep. 26, 1994 and assigned Ser. No. 08/312,388, and the other filed Jan. 21, 1997 and assigned Ser. No. 08/786,187) and makes use of this presentation in a unique analysis technique.

As discussed in the above-referenced co-pending applications, a self-assembled monolayer (SAM) including a species defining in part a nucleic acid strand (or other biologically-binding species, a nucleic acid strand exemplifying such species here), is made up of a mixture of a nucleic acid strand SAM-forming species and a species that is inert with respect to binding in which the nucleic acid strand is involved. Such an SAM can be formed on a surface by mixing the nucleic acid strand species and the inert species in a solvent and exposing the surface to the solvent. The relative amount of nucleic acid strand SAM-forming species in the solvent (and in the resultant SAM; the species' ratio in the solvent approximates or equals the species' ratio in the SAM) affects the average distance between individual nucleic acid strands presented at the surface; a higher ratio of inert species to nucleic acid strand species results in greater distance between nucleic acid strands in the SAM on the surface. It is generally advantageous to separate the individual nucleic acid strands from each other to an extent great enough to prevent inter-strand interaction, and interaction between other biological species coupled directly or indirectly to each strand, and sensitivity of a particular technique can be maximized by minimizing inter-strand distance on the surface (maximizing nucleic acid concentration). Generally, the molar ratio of the inert species to the nucleic acid species in the SAM is at least 70:30. According to a preferred embodiment, the molar ratio is at least 80:20, more preferably at least 90:10, and more preferably still at least about 95:5. In some cases, a molar ratio of inert species to nucleic acid species of about 99.5:0.5 is useful. A variety of spectroscopic techniques are available in the art for determining a final ratio of inert and nucleic acid species immobilized at a surface.

As mentioned, the major component in the SAM preferably is selected to expose, to the medium containing a target biological molecule, a functionality that inhibits NSB. Specifically, a functionality is selected to inhibit NSB of species present at relatively high concentration in a medium in which the biological molecule is presented to the surface. That is, the second species is selected among those that include chemical functionality, at the end of the molecule opposite the functionality that adheres to the surface, that does not bind species in the medium (the end opposite the functionality that adheres to the surface is presented to the medium, or "exposed" at the surface).

The second species has a formula X—R—NSBi, where NSBi is a NSB-inhibitor. NSBi can be selected from such groups as —$CH_3$; —OH; —$O(CH_2)_nH$, where n=1–15, preferably 1–7; —$CONH(CH_2)_nH$, where n=1–15, preferably 1–7; —$NHCO(CH_2)_nH$, where n=1–15, preferably 1–7; —$(OCH_2CH_2)_nH$, where n=1–15, preferably 1–7; —COOH; —$O(CH_2CH_2$—$O)_nH$ (where n=1–10); —$(CF_2)_nCF_3$, where n=1–20, preferably 1–8; olefins, and the like. Preferred are —$CH_3$, —OH, and —$O(CH_2CH_2$—$O)_nH$. According to a preferred embodiment in which a medium containing biological, particularly proteinaceous, species contacts the surface, the second species preferably has a formula X—R—O—$(CH_2CH_2$—$O)_n$—H, in which X represents a functional group that adheres to the surface, R represents a spacer moiety that promotes formation of a self-assembled monolayer of a plurality of the molecules, and n is from one to ten. According to a more preferred embodiment, n is from 2 to 5, and according to a particularly preferred embodiment, n is 3.

The surface, and the finctional group X that adheres to the surface, can be selected among a wide variety known to those of skill in the field of surface science. A nonlimiting exemplary list of combinations of surface materials and functional groups X suitable for use in the present invention follows. Although the following list categorizes certain preferred materials with certain preferred functional groups which firmly bind thereto, many of the following functional groups would be suitable for use with exemplary materials with which they are not categorized, and any and all such combinations are within the scope of the present invention. Preferred surface materials include metals such as gold, silver, copper, cadmium, zinc, palladium, platinum, mercury, lead, iron, chromium, manganese, tungsten, and any alloys of the above with sulfer-containing functional groups X such as thiols, sulfides, disulfides, and the like; doped or undoped silicon with silanes and chlorosilanes; metal oxides such as silica, alumina, quartz, glass, and the like with carboxylic acids; platinum and palladium with nitrites and isonitriles; and copper with hydroxamic acids. Additional suitable functional groups include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as a surface material in the present invention. Additional materials and functional groups suitable for use in the present invention can be found in U.S. Pat. No. 5,079,600, issued Jan. 7, 1992, incorporated herein by reference.

According to a more preferred embodiment, a combination of gold as surface material and a functional group X having at least one sulfer-containing functional group such as a thiol, sulfide, or disulfide is selected. The interaction between gold and such sulfer-containing functional groups is a well-studied science, and a nonlimiting representative exemplary list of such sulfer-containing functionalities may be found in an article entitled "Wet Chemical Approaches to the Characterization of Organic Surfaces: Self-Assembled Monolayers, Wetting and the Physical-Organic Chemistry of the Solid-Liquid Interface", by G. W. Whitesides and Paul E. Laibinis, Langmuir, 6, 87 (1990), incorporated herein by reference. Particularly preferred in the present invention is a gold surface, and a thiol as functional group X.

The spacer moiety R can be selected from among organic spacer moieties that promote formation of self-assembled monolayers. Such moieties are well-known to those of ordinary skill in the art, as described in the above-referenced articles by Laibinis, et al. *Science* 245, 845 (1989), Bain, et al. *J. Am. Chem. Soc.* 111, 7155–7164 (1989), and Bain, C, et al. *J. Am. Chem. Soc.* 111, 7164–7175 (1989). Preferred moieties R are hydrocarbon chains optionally interrupted by hetero groups, of a length of at least eight carbon atoms. As used herein, "hydrocarbon" is meant to define includes alkyl, alkenyl, alkynyl, cycloalkyl, aryl, alkaryl, aralkyl, and the like. Hetero groups can include —O—, —CONH—, —CONHCO—, —NH—, —CSNH—, —CO—, —CS—, —S—, —SO—, —$(OCH_2CH_2)_nR$ (where n=1–20, preferably 1–8), —$(CF_2)_n$—(where n=1–20, preferably 1–8), olefins, and the like. It is important that the R is a self-assembled monolayer-promoting moiety. Whether or not a particular moiety promotes formation of a self-assembled monolayer can be routinely determined by one of ordinary skill in the art, optionally in accordance with the teachings of the preceding references, using for example surface spectroscopic techniques.

According to a preferred embodiment, R=—$(CH_2)_n$—, where n is from about 8 to about 24, preferably from about 10 to about 20, most preferably from about 9 to about 16. According to an embodiment of the invention in which R is a moiety in the group X—R—Ch, R preferably comprises —$(CH_2)_n$—$O(CH_2CH_2$—$O)_m$—, where n=4–20, preferably 8–14, and m=1–10, preferably 2–5. a variety of moieties R can be used on different molecules forming a self-assembled mixed monolayer, so long as other requirements described herein are met.

R should also be selected to be chemically stable to reagents used in the synthesis of a species into which it is incorporated. For example, if the species is formed by cleavage of a disulfide, R should be stable to reagents such as mercaptoethanol and dithiothreitol.

The metal ion is preferably selected from those that have at least four coordination sites, preferably six coordination sites. a non-limiting list of metal ions suitable includes $Co^{3+}$, $Cr^{3+}$, $Hg^{2+}$, $Pd^{2+}$, $Pt^{2+}$, $Pd^{4+}$, $Pt^{4+}$, $Rh^{3+}$, $Ir^{3+}$, $Ru^{3+}$, $Co^{2+}$, $Ni^{2+}$, $Cu^{2+}$, $Zn^{2+}$, $Cd^{2+}$, $Pb^{2+}$, $Mn^{2+}$, $Fe^{3+}$, $Fe^{2+}$, $Au^{3+}$, $Au^+$, $Ag^+$, $Cu^+$, $MO_2^{2+}$, $Tl^{3+}$, $Tl^+$, $Bi^{3+}$, $CH_3Hg^+$, $Al^{3+}$, $Ga^{3+}$, $Ce^{3+}$, $UO_2^{2+}$, and $La^{3+}$.

The chelating agent is preferably selected from bidentate, tridentate, and quadradentate chelating agents, and is selected in conjunction with the metal ion so that when the chelating agent coordinates the metal ion, at least two free coordination sites of the metal remain. The chelating agent and metal are selected so that the chelating agent can coordinate the metal ion with a degree of stability great enough that the metal ion will remain immobilized at the surface by the chelating agent.

Additionally, the chelating agent is selected as one that has a chelating moiety and a non-chelating linker moiety, such that it can be covalently linked via its linker moiety to the spacer moiety R while leaving the chelating moiety undisturbed by the covalent linkage and free to coordinate a metal ion. Alternatively, the chelating agent can be selected as one that can be modified via routine organic synthesis to include a non-chelating linker moiety, if such synthesis leaves undisturbed the chelating moiety. One of ordinary skill in the art will appreciate that the non-chelating linker moiety should provide functionality suitable for chemical linkage such as, for example, an amine, alcohol, carbamate, carboxylic acid, thiol, aldehyde, olefin, etc., for formation of in an ester linkage, formation of an amide linkage, thiol displacement and this ether formation, and the like.

With the above considerations in mind, suitable chelating agents and corresponding metal ions can be selected by those of ordinary skill in the art. In accordance with such selection reference can be made to "Chelating Agents and Metal Chelates", Dwyer, F. P.; Mellor, D. P., Academic Press, and "Critical Stability Constants", Martell, a. E.; Smith, R. M., Plenum Press, New York. These works describe a variety of chelating agents, and discuss the stability of coordination between chelating agents and metal ions. Preferably, a chelating agent and metal ion is selected such that the disassociation constant of the combination in aqueous solution is better than 10 nM at physiological pH, that is, such that at least one half of the metal ions are coordinated by chelating agent at a concentration of 10 nM.

A non-limiting exemplary list of suitable chelating agents includes nitrilotriacetic acid, 2,2'-bis(salicylideneamino)-6, 6'-demethyldiphenyl, and 1,8-bis(a-pyridyl)-3,6-dithiaoctane.

In some cases it may be advantageous to test a particular chelating agent/metal ion pair to determine whether coordination will be sufficiently stable for use in the present invention. It is within the realm of routine experimentation to one of ordinary skill in the art to follow the teachings herein to immobilize a chelating agent at a surface, such as at a gold SPR chip surface, and then to test the interaction between the chelating agent and the metal ion via, for example, SPR spectroscopy under various conditions. In addition, preliminary screening can be carried out by reacting a prospective chelating agent and metal ion in solution and analyzing the solution spectroscopically. In this regard, reference can be made to, "Spectroscopy and Structure of Metal Chelate Compounds", Nakamoto, K.; McCarthy, S. J., Wiley, New York.

According to one aspect of the invention, an article suitable for capturing a biological molecule is provided. The article includes a self-assembled mixed monolayer of a first species and the second species as described above. The first species has a formula X—R—Ch—M—BP, where X, R, Ch, and M are as described above, and BP is a binding partner of a biological molecule, coordinated to the metal ion.

According to a preferred embodiment the binding partner includes a recognition region for the biological molecule, and a polyamino acid tag that can coordinate the metal ion and that is remote from the recognition region. a polyamino acid tag is meant to define a series of amino acids in proximity such that they can coordinate the at least two free coordination sites of the metal ion. According to a one embodiment, from 2 to about 10 neighboring amino acids such as, for example, neighboring histidines, lysines, arganines, glutamines, or any combination of these can serve as a polyamino acid tag. According to a preferred embodiment, the polyamino acid tag includes at least two, and more preferably from two to 10 neighboring histidines, and according to a particularly preferred embodiment the polyamino acid tag includes from about 3 to about 8 neighboring histidines. With reference to the above-identified work entitled, "Critical Stability Constants" (Martell, et al), selection of these and additional amino acids can be made in conjunction with selection of a metal ion M.

A variety of vectors that express proteins or fragments thereof containing a histidine tag are commercially available from, for example, Novagen, of Madison, Wis. However, these vectors are designed to code proteins or fragments for metal chelate affinity chromatography. For purposes of metal chelate affinity chromatography, it is not important where on the vector the histidine tag lies. The purpose of the histidine tag in that application is solely to allow the chromatography solid phase to adsorb the protein. Therefore, it is not a priority in the commercialization of histidine-tagged proteins that the tag be placed at a location remote from the recognition region.

Where the binding partner is a polyamino acid, a polyamino acid tag can be expressed at a desired location (remote from the recognition region) in a number of ways known to those of ordinary skill in the art, for example by employing the polymerase chain reaction (PCR) to incorporate a nucleic acid sequence that encodes the polyamino acid tag at the appropriate position. Placement of a polyamino acid tag at a desired location is discussed more fully below.

Modification of a protein or fragment thereof by applying to the protein or fragment a polyamino acid tag at a location remote from the recognition region of the protein or fragment can be accomplished readily by one of ordinary skill in the art using, for example, recombinant technology. According to one method for such modification, a desired protein is grown from DNA that codes for the protein, and an expression vector. The protein is isolated and truncated at various amino acid positions, and the protein's specific active sequence (recognition region) elucidated by randomly mutating the resultant sequences. Alternatively, via sequence homology, a variety of similar proteins that recognize slightly different species are identified and their amino acid sequences determined. The various sequences are compared using a computer, and regions that are variable between the various proteins identified as recognition regions.

Subsequently a strand of DNA for a the desired protein fragment that is large enough to correctly fold can be sequenced with a polyamino acid tag at a location remote from the recognition region. DNA sequencing is routine in the art via, for example, PCR. With an expression vector, the desired polyamino acid-tagged protein fragment then can be readily grown and isolated.

The desired fragment will coordinate to the metal ion via the polyamino acid tag, and the recognition region, remote from the tag, will not face the surface, but will be exposed to the medium containing or suspected of containing the binding partner of the protein fragment. As used herein, the term "remote" is meant to define a situation in which the polyamino acid tag is separated from the recognition region by a distance of at least about 20 amino acids, preferably at least about 40 amino acids.

The polyamino acid tagging technique of the invention can be applied to a variety of polyamino acids such as proteins, antibodies, antigens, polymers, and ligands.

Where the binding partner is a not a polyamino acid, it can be coupled chemically, for example covalently coupled, to a polyamino acid including a polyamino acid tag. In this case the coupling of the polyamino acid is effected on the binding partner at a location remote from the recognition region, and/or the polyamino acid that is coupled to the binding partner has a tag at a location remote from the location of coupling to the binding partner. Synthesis of such a species would be routine to those of ordinary skill in the art.

The present invention also provides a SAM-forming species that includes, at least in part, a nucleic acid strand, and can include double-stranded nucleic acid. The SAM-forming species according to this aspect of the invention when defining, in part a SAM on a surface of an article, can define a sensing element suitable for use in a biosensor, and especially for use in determining a binding partner of a nucleic acid strand. Accordingly, the invention provides, in one embodiment, a species X—R—NA, or X—R—NA—NAB, as defined below. In another embodiment the invention provides a sensing element including a substrate and a self-assembled monolayer of a species X—R—NA, or X—R—NA—NAB, adhered to the surface of the substrate. The SAM contains, in preferred embodiments, one of these species in combination with an inert, non-binding thiol as discussed above in combination with the species X—R—R—Ch, etc. The substrate preferably includes a metal surface, such as can be provided by a film of metal on a non-metal substrate. In this set of embodiments, X represents a functional group that adheres to the surface, R represents a spacer moiety that promotes formation of a self-assembled monolayer of a plurality of the species, NA represents a nucleic acid strand, and NAB represents a nucleic acid strand that is a binding partner of NA. NA or NAB can be a binding partner of a biological molecule to be determined.

Figure 8:
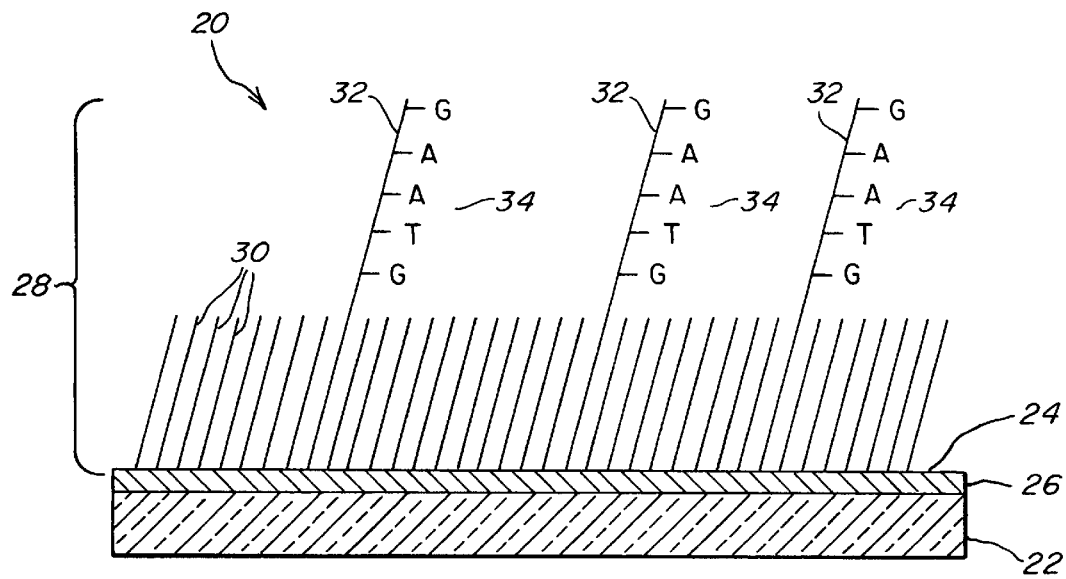
FIG. 8 is a schematic illustration of a surface derivatized with a mixed SAM formed of an inert major component and a minor component that includes a nucleic acid strand.
Figure 9:
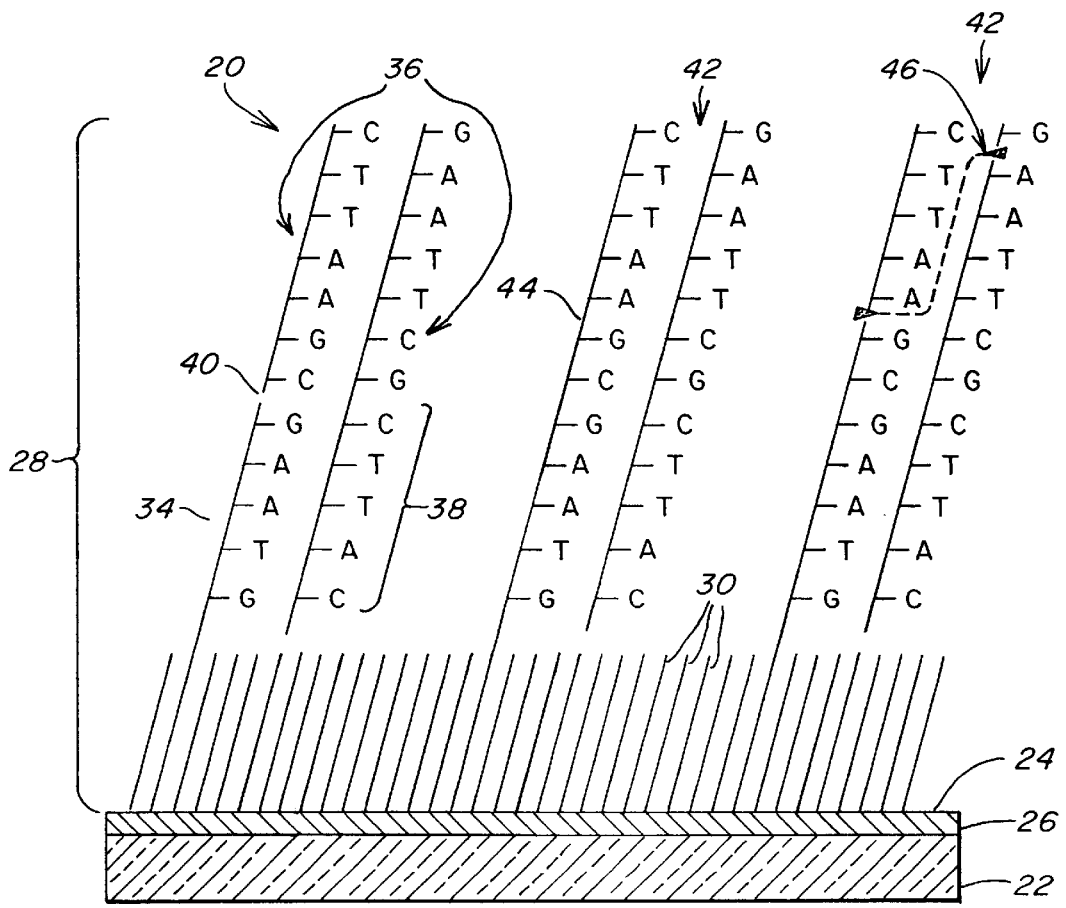
FIG. 9 is a schematic illustration of the SAM of FIG. 8 following hybridization with double-stranded DNA having a "tail" complementary to the nucleic acid strand presented by the surface after hybridization, ligation, and restriction.
Figure 10:
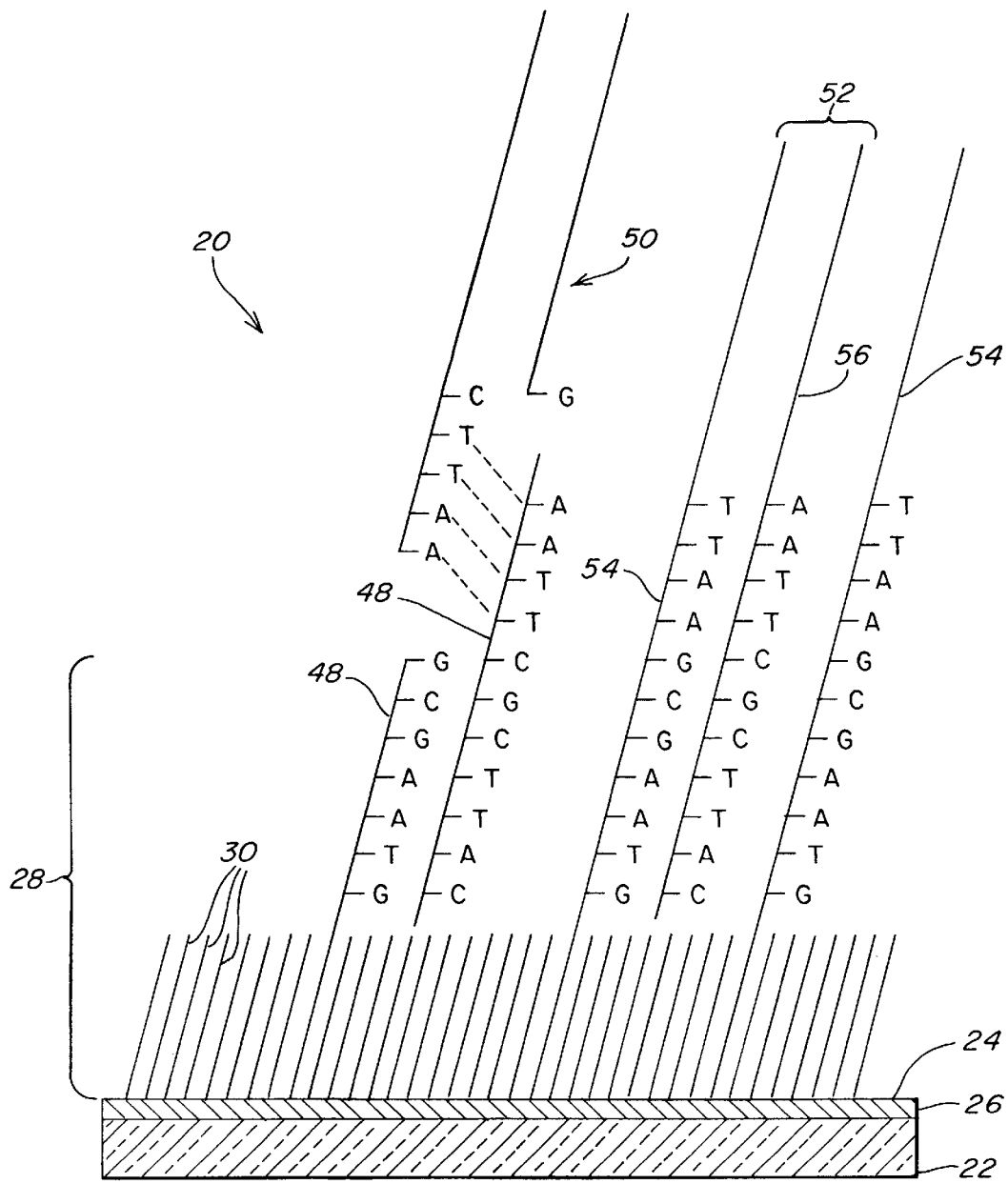
FIG. 10 is a schematic illustration of hybridization of double-stranded DNA, ligated with the same restriction enzyme used to ligate the double-stranded DNA immobilized at the surface, to the DNA of the surface followed by ligation and disassociation.

Referring now to FIGS. 8–10, SAMs including the species X—R—NA and X—R—NA—NAB are illustrated schematically. A description of this aspect of the invention is provided in greater detail below in Examples 10–14, and a brief description is provided here.

Referring to FIG. 8, an article 20 is illustrated which can define an SPR chip in one embodiment. Article 20 includes a substrate 22 having a surface 24 upon which is provided a SAM. In the embodiment illustrated, substrate 22 includes a film 26 on a surface thereof, the exposed surface of film 26 defining surface 24 of the overall substrate arrangement. Where an SPR chip is provided, substrates 22 can be glass and film 26 can be a thin gold film. A SAM 28 is provided on surface 24 of the substrate and includes a major component species 30 and a minor component species 32 which is a SAM-forming species including a nucleic acid strand 34. Nucleic acid strand 34 is preferably covalently coupled to a self-assembled monolayer-forming species X—R which forms a self-assembled monolayer with minor component 30. Minor component 30 is selected to have the ability to form an SAM with nucleic acid strand SAM-forming species 32, is preferably of a length short enough, relative to species 32, that nucleic acid strand 34 of species 32 is exposed for hybridization, and otherwise can include a chemical functionality, exposed away from surface 24, that is desirable for whatever purpose article 20 serves. Typically, minor component 30 will include an NSB-minimizing species such as a species terminating in polyethylene glycol. Synthesis of species 30 and species 32 is described below in the examples. The mixed monolayer including species 30 and species 32 includes nucleic acid strands 34 that are biologically isolated from all other nucleic acid strands. In particular, at least 90% of nucleic acid strands 34 are biologically isolated from other nucleic acid strands. As used herein, the term "biologically isolated" is meant to define a situation in which, were the nucleic acid strands complementary to each other, they would hybridize or interact in another way. "Biologically-isolated" is also meant to define a situation in which if one nucleic acid strand included a region specific for a protein, and a protein were immobilized at that strand, if a neighboring nucleic acid strand had a sequence for that protein, the protein would not interact biologically (via biological binding or other recognition) with that strand. Specifically, at least 90% of nucleic acid strands 34 are isolated from all other nucleic acid strands, preferably by inert SAM-forming species 30, by at least 5 nm.

Article 20 can be used for a variety of purposes in which it is advantageous to expose a single-stranded nucleotide at a surface. In one preferred embodiment, with reference to FIG. 9, double-stranded nucleic acid (e.g. double-stranded DNA, dsDNA, as referred to hereinafter) 36, one of the strands having a "tail" 38 that is complementary to nucleic acid strand 34 covalently immobilized at surface 24, is exposed to the surface and dsDNA 36 hybridizes to strand 34 via tail 38.

Thus, a single nucleic acid strand is provided that can be covalently linked to surface 24. As used herein, "covalently" is meant to define linkage that is stronger, chemically, than non-covalent linkage such as Van der Waals interactions, ionic interactions, coordinate bonding, and the like. Linkage of species such as X at an appropriate surface, for example thiol linkage to gold, is covalent. The use of component 30 allows nucleic acid strands 34 to be presented at the surface while free of interaction with any neighboring nucleic acid strands. This allows freer access to binding, recognition, and other interaction.

The "nick" 40 in the nucleic acid strand can be mended with DNA ligase enzyme, resulting in immobilized dsDNA species 42 covalently attached to surface 24 via strand 44 extended in the course of the hybridization/ligating step described. When the dsDNA is selected to contain a restriction enzyme site, a restriction enzyme 46 can be used to cut the dsDNA 42. Referring now to FIG. 10, the resulting cut, surface-immobilized dsDNA species 48 can be ligated with any dsDNA that has been cut also with restriction enzyme 46. As illustrated, dsDNA 50 can be hybridized to species 48 and the "nicks" mended with DNA ligase, resulting in surface-immobilized, dsDNA 52 including covalently-immobilized strand 54 and strand 56 which is immobilized via hybridization to strand 54. The "antisense" strand 56 can be dissociated with heat or chemical treatment to expose ssDNA 54 for hybridization studies. Of course, in FIG. 10 strands 54 and 56 include nucleic acids that are not represented throughout the length of each strand.

Thus, the embodiment of the invention represented in FIGS. 8–10 includes a single nucleic acid strand immobilized, preferably covalently immobilized, at a surface and not removable from the surface under disassociation conditions. As used herein, the term "disassociation conditions" is meant to define a situation in which, where a single strand 54 is covalently immobilized at the surface and a complementary strand 56 is hybridized to strand 54, strand 56 can be removed. These conditions include hot water, mild chemical treatment, and other techniques available to those of ordinary skill in the art. The invention also includes single strand 54 immobilized to the surface and not removable therefrom under disassociation conditions, and complementary strand 56 hybridized to strand 54 and removable from the surface under disassociation conditions.

Single-stranded or double-stranded nucleic acid can be used to bind, at the surface, biological binding partners that are partners of the immobilized strand or strands, and used in further study. For example, a binding partner of an immobilized strand or strand can be immobilized at the surface, and can serve as a binding partner of yet another biological binding partner that then is immobilized, and that species used in studies.

Attachment of a wide variety of nucleic acid strands NA to a moiety R, for example in a way that the strand can biologically bind to its nucleic acid binding partner NAB, can be accomplished with reference to the teaching of examples 10–14, below. It is to be understood that the procedure given in the examples for the preparation of a DNA chip may be applied to the preparation of any nucleic acid chip, such as an RNA chip. Such a chip can be used to detect DNA hybridization (human genome project, diagnostic scanning of DNA for genetic mutants), to present DNA-binding proteins for the study of subsequent protein-protein interactions for which DNA binding is a critical element of the interaction, using instruments such as SPR devices, or to build an easy analysis DNA computer.

The articles of the present invention can be used for a variety of applications, including biosensing applications, test assays, and the like. The term "test assay" generally refers to any procedure in which a member of a biological binding partner pair is to be captured from a medium in which it is dispersed. For example, "test assay" may be used to describe a diagnostic procedure, analytical procedure, microanalytical procedure, forensic analysis, pharmacokinetic study, cell sorting procedure, affinity chromatogram, industrial or laboratory recovery or analysis of one or more species such as toxins, catalysts, or starting materials or products, and the like. a typical test assay is an immunoassay. Biosensing applications include those such as drug screening, environmental monitoring, medical diagnostics, quality control in the pharmaceutical and food industries, and other areas in which it is advantageous to sensitively determine biological binding between partners.

The present invention also provides a method of making an article having a surface for capturing a target molecule. The method involves formulating a solution containing a mixture of at least two self-assembled monolayer-forming species as described herein, and exposing to the surface the solution for a period of time sufficient to form a self-assembled monolayer on the surface. The amount of time required to allow the monolayer to spontaneously chemisorb to the surface will vary depending upon the solvent, the surface, and the monolayer-forming species. Typically, the time required will be on the order of hours, and often a 24-hour exposure is carried out to make certain that maximal coverage is obtained. The degree of formation of a monolayer can be determined by routine spectroscopic methods, as well as physical method in some cases, such as contact angle measurements and the like.

Other methods for forming the monolayer on the surface are included, for example those disclosed in copending application Ser. No. 08/131,841, filed Oct. 4, 1994 and entitled, "Formation of Microstamped Patterns on Surfaces and Derivative Articles", incorporated herein by reference.

The embodiment of the invention that involves a SAM-forming species including a nucleic acid strand (or multiple nucleic acid strands) can be used: 1) to detect DNA hybridization (human genome project, diagnostic scanning of DNA for genetic mutants), 2) to present DNA-binding proteins for the study of subsequent protein-protein interactions for which DNA binding is a critical element of the interaction, using instruments such as SPR devices, 3) to build an easy analysis DNA computer. Additionally, both the species X—R—Ch and the species X—R—NA can be used in ultra high through put devices to detect interactions by monitoring the time dependence of electron transfer from bait to prey. The biospecific species self-assemble on a surface such as a metal surface, such as a gold-coated electrode. A peptide or DNA library is generated such that it is also attached to a metal. Specifically, a mixed self-assembled monolayer can be first formed on a gold substrate. The major component is an inert tri-ethylene glycol terminated thiol and the minor component terminates in a photolabile group. Using previously-described masking techniques, a DNA or peptide library is generated such that the spatial address of each species is known. The surfaces are brought into close proximity (atomic force microscopy; AFM technology) so that electrons generating from the goldtipped electrode travel through a known species immobilized on the electrode via, for example, SAM formation, to a second metal surface, through the surface immobilized library components (peptides or DNA) if and only if there is biological binding between the two. The transfer of electrons from the electrode through individual components of the library can be monitored by a detection array beneath the metal of the library support. Alternatively, a direct interaction can be gleaned from the time dependence of conductance returning to the electrode when an alternating current is applied. The minor component of the self-assembled monolayers can be phenyleneethynylene thiolates in this embodiment since it has been shown that they have higher conductance than alkanethiolates. However, the two thiols when mixed will form an ordered SAM (See, e.g., *Science*, "Are Single Molecular Wires Conducting?", Vol. 271, 1996, pgs. 1705–1707).

Figure 11:
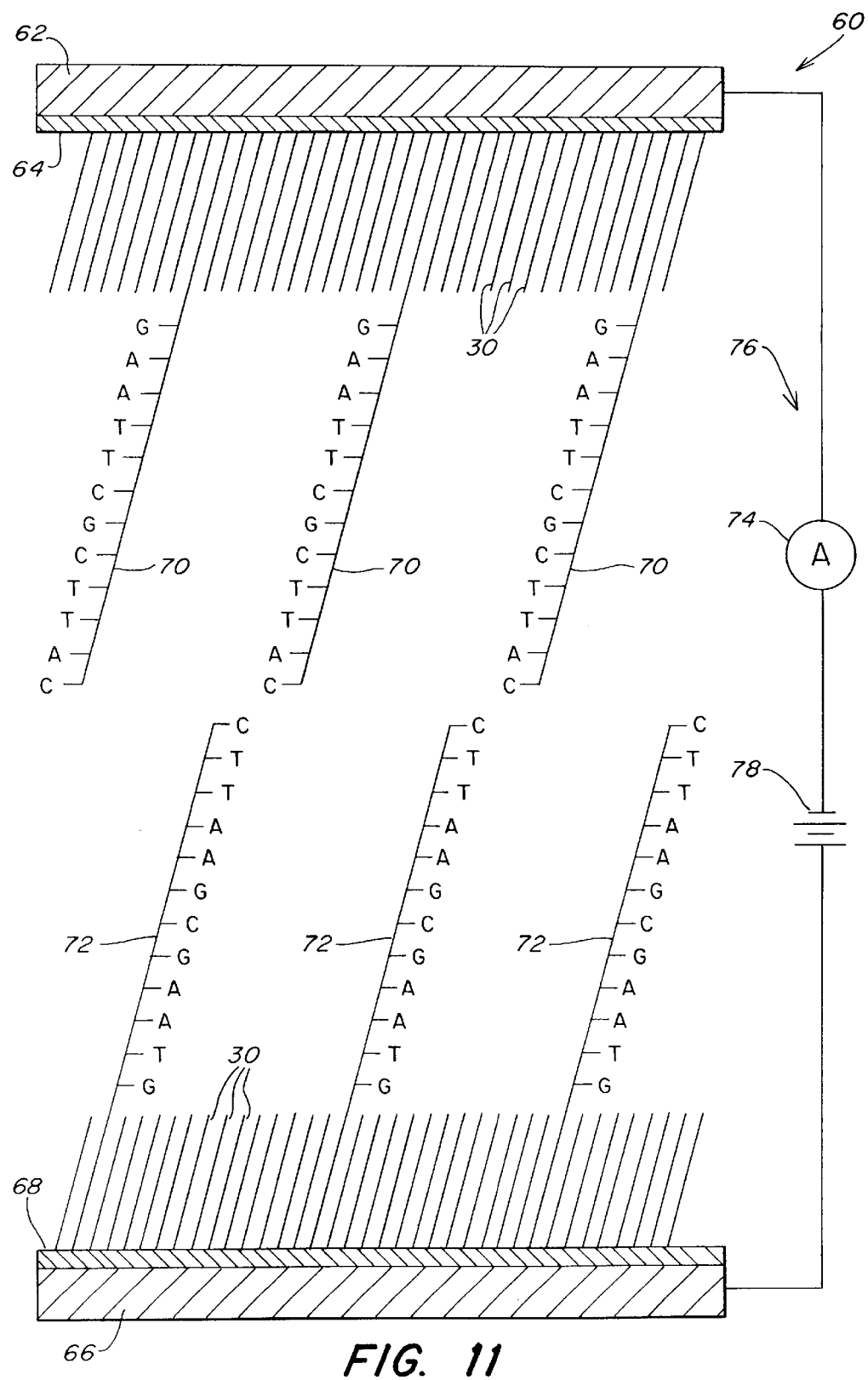
FIG. 11 is a schematic representation of nucleic acid strands 72 as part of a SAM on an electrode 66 and complementary nucleic acid strands 70 as part of a SAM on electrode 62 with an electrical circuit including the electrodes.

Referring now to FIG. 11, an electronic biological binding detector system 60 is illustrated schematically, including a first electrode 62 having a surface 64, a second electrode 66 having a surface 68, and an external electrical circuit 70 including a potential source 72 and Ammeter 74 electrically connecting electrodes 62 and 66. Each of electrodes 62 and 66 can be made of a material. that also defines surfaces 64 and 68, or can be made of any electrically-conducting material that is coated with a film of material defining surfaces 64 and 68. Where an auxiliary film of material defines surfaces 64 and 68, if the film is thin enough it need not be extremely conductive electrically. In preferred embodiments electrodes 62 and 66 are formed of relatively inexpensive, electrically-conductive material and surfaces 64 and 68 are defined by films of gold. Alternatively, the electrodes can be defined by a supporting substrate of non-conducting material such as glass and coated with a thin film of conductive material such as gold defining surfaces 64 and 68, the films of gold connected to electrical circuit 70.

Each of surfaces 64 and 68 carries a SAM of a major, inert component 30 and a minor, nucleic acid component. Electrode 62 is a probe and carries a SAM including nucleic acid species 70, the sequence of which is known. Surface 68 of electrode 66 carries a SAM including a nucleic acid species 72, a sequence of which is unknown.

Figure 12:
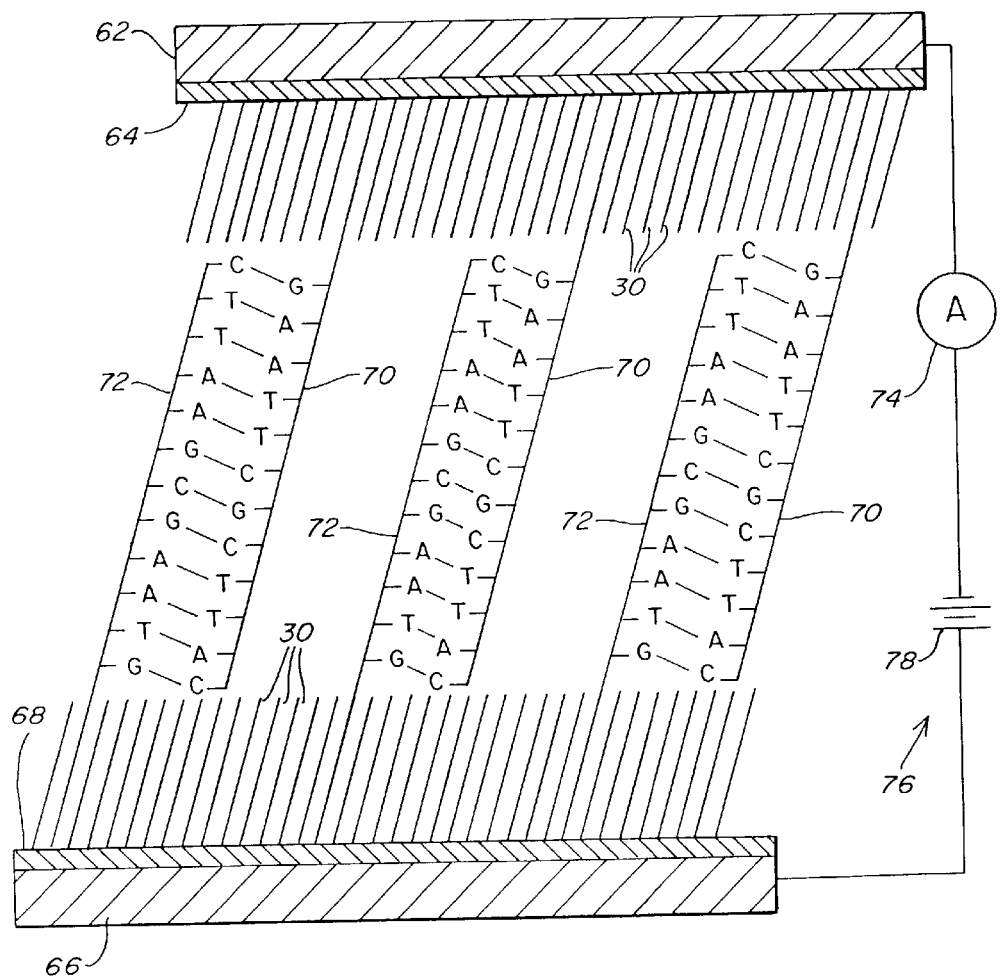
FIG. 12 is a schematic illustration of the arrangement of FIG. 11 in which complementary nucleic acid strands 70 and 72 are hybridized, completing an electrical circuit.

When surfaces 64 and 68 of electrodes 62 and 66 are brought into proximity close enough for interaction of nucleic acid strands 70 and 72, for example via AFM, if strand 72 is the complement of strand 70, then hybridization will occur and if the strands are not complementary then hybridization will not occur. Because electron transfer proceeds through hybridized nucleic acid (dsDNA) much faster than through ssDNA, where strands 72 and 70 hybridize, Ammeter 74 will register a distinguishable current flow. This is illustrated in FIG. 12, where strands 70 and 72 are complementary, thus electron transfer can occur to a relatively high degree through the strands and between electrodes 62 and 66. Although electronic circuit 70 is illustrated schematically as a D.C. circuit, an A.C. circuit can be used.

Figure 13:
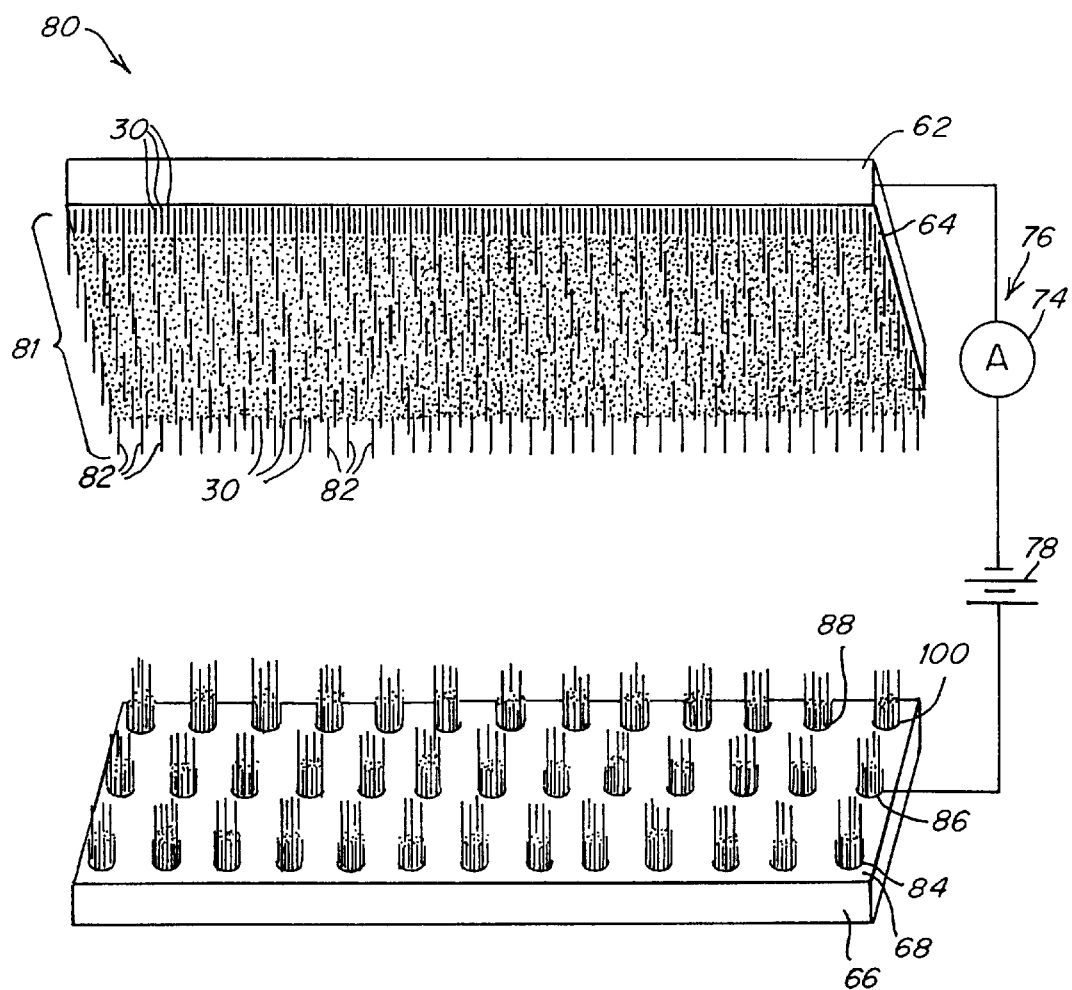
FIG. 13 is a schematic illustration of an array of different biological species immobilized at one electrode, and an array of similar biological species immobilized at another electrode, for use in electron transfer probe analysis.

Referring now to FIG. 13, a detection array 80 is illustrated schematically and includes, like system 60, electrodes 62 and 66 having electrode surfaces 64 and 68 upon which SAMs are formed, and external electrical circuit 70. On surface 64 of electrode 62 is formed a SAM 81 of probe ssDNA 82 and inert, major component 30. On surface 68 of electrode 66 is a plurality of regions 84, 86, 88, 100 . . . that together define a matrix of different nucleic acid strands. Each region 84, 86 . . . can be defined by a portion of an overall, continuous SAM across electrode surface 68 (not shown), or can be defined by an isolated SAM island. Each of these arrangements can be constructed in a different manner but may be essentially identical where islands are formed and the intervening regions of the islands filled in with inert species 30. That is, formation of islands and filling in intervening regions with the inert species results in a continuous SAM. In another embodiment, however, individual islands 84, 86, . . . may be defined by individual regions of patterned gold on the surface 68, the gold regions separated from each other by non-SAM-promoting regions. In this way, discrete islands of SAMs can be formed, separated by areas not carrying any SAM, each SAM being, distinct from each other SAM.

In this embodiment, each individual region 84, 86, 88, 100 . . . is addressed by individual electronic circuitry. The illustration is representative in that circuitry addressing region 86, only, is illustrated. When surface 64 is brought into proximity with surface 68, allowing interaction between single nucleic acid strands 82 in SAM 81 of electrode 62 and the SAMs on surface 68 of electrode 66, where the nucleic acid strands hybridize, detectable electron transfer between individual the regions of electrode 66 and electrode 62 can be determined. Accordingly, one or more regions 84, 86, 88, 100 . . . can be identified as carrying nucleic acid strands complementary to the probe nucleic acid 82 presented by electrode 62.

The array of different regions 84, 86, 88, 100 . . . of electrode 66 can be fabricated in a variety of ways. According to one technique individual islands of a SAM-promoting material are formed on a non-SAM-promoting surface via photolithography, or other known techniques including etching techniques described in U.S. Pat. No. 5,512,131, referenced above. In the latter technique a SAM-promoting film, such as a gold film, is deposited on a substrate such as glass, a patterned SAM is formed on the gold surface via "microcontact printing" ("microstamnping"), and regions of the gold film not covered by the patterned SAM are etched. Removal of the SAM exposes patterned, isolated gold islands on glass. Alternatively, the microstamped SAM pattern can define regions desirably etched, intervening regions (defining the gold islands desirably preserved) are filled in with a different SAM, and an etchant applied to which the latter-added SAM covering the islands is resistant. Other combinations of techniques for such a process are described in commonly-owned international patent publication no. WO 96/29629, published Sep. 26, 1996, incorporated herein by reference.

In another technique, an array of different SAMs on surface 68 of electrode 66 can be formed by creating a SAM including exposed photolabile groups and, via standard lithographic techniques, creating an array of SAMs as described. In another technique, as described more fully in copending, commonly-owned application Ser. No. 08/616, 929, referenced above, an array of SAMs on surface 68 of electrode 66 can be created by positioning a contoured surface of an article against surface 68, the contoured surface creating thereby a series of channels alternating with "blocked" regions on the surface, and filling the channels with a fluid containing a desired SAM-forming species. Manipulation of the article, and use of different articles and different orientations, as described in the referenced application, can result in creation of the patterned SAM.

The electron transfer detection array is not limited to detection of interaction between nucleic acids, but can be used for any of a wide variety of biological interactions. For example, an array of ssDNA or dsDNA can be created as described, the DNA having a binding region specific for a particular biological molecule such as a protein, and in this manner an array of proteins can be presented on the surface for electron-transfer probing with known species on electrode 62.

Similarly, an array of different species X—R—Ch—M—BP can be formed on surface 68 of electrode 66, a variety of different biological binding partners can be presented at different regions 84, 86, 88, 100 . . . , and region-specific, electron-transfer determination made based upon biological binding between species in the individual, isolated regions of electrode 66 and species presented at surface 64 of the electrode 62.

One particularly suitable application for the species X—R—NA or X—R—NAB, and a chip carrying a SAM of one or more of these, is the study of interacting proteins and protein-DNA complexes that regulate gene transcription. Large soluble yeast PolII holoenzyme/mediator complexes must communicate with some other DNA-bound complex to effect transcription. Precise and accurate determination of interactions of these large complexes with DNA-bound transcription factors would be advantageous, and can be accomplished with the technique of the present invention.

In accordance with an embodiment of the invention in which an article has a surface with a monolayer of X—R—

Ch—M adhered thereto, M can serve as a binding partner to capture species that adhere to M. An exemplary list of such species is disclosed in U.S. Pat. No. 5,250,188, issued Oct. 5, 1993 to Bruening, et al. and incorporated herein by reference.

In all of the embodiments of the invention in which an article is provided, a substrate also may be included in the article. The substrate typically will support a film of material that defines the surface, on a side of the film opposite the side at which a self-assembled monolayer is formed.

The biospecific SAMs described herein afford several advantages that make the technique of this example sensitive and practical: 1) they self-assemble on metal-one of the factors necessary for electron conduction; 2) because they are mixed monolayers with the biospecific thiol being the minor component, the ligands of interest can be immobilized far enough from each other that electron transfer will not occur radially in the plane of the electrode surface which would compromise and complicate results; 3) the rigid structure of a SAM ensures that the immobilized ligands are held a fixed distance from the electrode which is important because measurements of the electron transfer rates depend on the distance the electrons travel; 4) the biospecific SAMs control the orientation of the immobilized molecule (active site or DNA orientation), clear advantage over random coupling procedures that would put the site of interaction at varying distances from the electrode complicating and compromising results; 5) biospecific SAMs provide a universal acceptor surface to which any unmodified oligo or histidine-tagged protein can be attached. 6) the aliphatic chain of the biospecific thiol can be modified (Bumm, L. A., Arnold, J. J., Cygan, M. T., Dunbar, T. D., Burgin, T. P., Jones, L. II, Allara, D. L., Tour, J. M., Weiss, P. S., Are single molecular wires conducting?, *Science* 271 (1996) pp. 705–707) so that it is much more conducting than the inert major component thiols thus giving a greater signal:noise ratio. Phenylene-ethynylene benzothiolates have been shown by Bumm, et al. to be much more conductive than alkanethiolates. Mixed SAMs of the two species could be formed. The described array-array interface system can easily be scaled up giving ultra high through-put detection.

In the embodiments discussed and illustrated above, in particular in connection with FIGS. 8–13, electron transfer is used as a tool to determine biological binding. In another set of embodiments applicable to the systems illustrated in FIGS. 8–13, an electronic property not necessarily defined by electron transfer can be used to determine biological binding and other chemical interaction. For example, the systems illustrated in FIGS. 8–13 can involve, rather than direct current probing across biological molecules, alternating current probing of the molecules for determination of a shift in phase of alternating current applied to the system. In the embodiments illustrated, power source 72 would be replaced by a source of alternating current, and ammeter 74 would be replaced by a phase detector.

Figure 14:
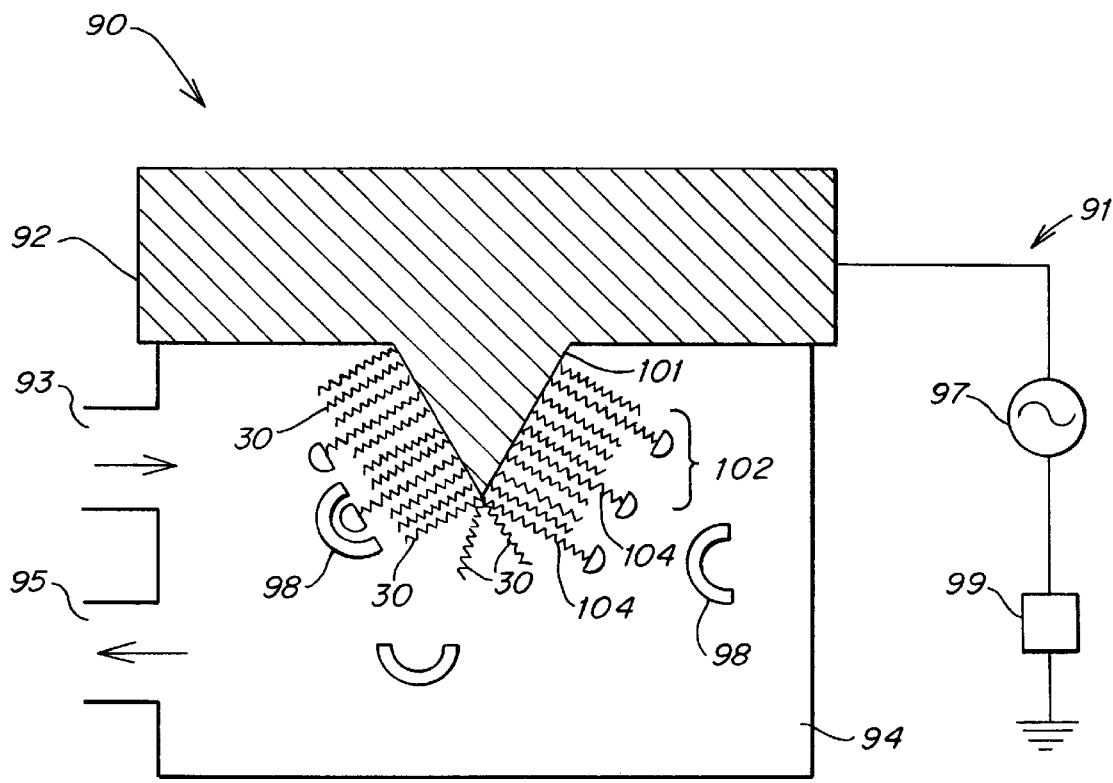
FIG. 14 is a schematic illustration of a single-electrode electronic property probe for biological molecules.

One system 90 for electronic-property probing of molecules is illustrated schematically in FIG. 14. System 90 is a one-electrode system including an electrode 92 and a container 94 defining an enclosure, one surface of which is defined by a surface of electrode 92. Container 94 includes, as illustrated, a fluid inlet 93 and a fluid outlet 95. Container 94 need not be a fluid enclosure, as illustrated, but need only be capable of positioning a medium containing a target species 98 in proximity of electrode 92. Electrode 92 includes a surface 100 upon which is a SAM 102 including NSB-minimizing species 30 and species 104 defined by a species X—R—Ch, X—R—Ch—M—BP, X—R—NA, all as described above, or any other SAM-forming species terminating in a chemically or biologically-active species. "Chemically or biologically active species", as used herein, is meant to include proteins, enzymes, nucleic acids, species that engage in phosphorylation or hydrolysis, species that undergo conformational changes, photochemically-active species, electrochemicallyactive species, and the like. The ratio of species 104 to 30 can be as described above. Species 104 terminates in the chemically or biochemically active species, that is, the end of species 104 facing away from the surface 100 of electrode 92 terminates in the actives species.

Electrode 92 can be a STM tip, or the like. The electrode can be gold-coated with thiol-end group containing SAM-forming species defining SAM 102.

Target species 98 introduced into container 94 can be any analyte of interest, for example a protein, DNA, RNA, other nucleic acid, small molecule, catalyst such as enzymes, affector molecule, and the like. The medium within which target species 98 is carried can be a fluid selected solely for the purpose of delivering the target molecule to the electrode, or the medium can have electrical conductivity or resistivity if desired. It can be useful for the fluid medium to be conductive in the case of all DNA hybridization. Electrically-nonconductive fluid media would be useful in a phase-shift detection system where the particular degree of conductivity can be selected for a particular application.

Species 104 and species 98 are chemically or biochemically active with respect to each other. Thus, when a reaction is allowed to take place involving species 104 (for example biological binding between target species 98 and species 104), a change of an electromagnetic property of the system results. For example, if species 104 and 98 are protein/protein, protein/DNA, or DNA/DNA (including other nucleic acid binding partners), and if binding occurs, or where species 98 is a species that causes a structural or chemical modification of immobilized species 104, then detection can be made by applying an alternating current to the electrode and monitoring changes in electromagnetic properties of the system such as changes in voltage, current or impedance as a function of frequency and/or temperature. Binding of species 98 to species 104, or a chemical or structural change of species 104 caused by species 98 will cause a characteristic detectable electrical property signal in the system such as a change in impedance or dielectric value.

As illustrated, the system includes an external electrical circuit 91 including a source 97 of alternating current, and an impedance sensor 99. The system is grounded. The impedance sensor can be a current sensor in parallel with circuit 91, or another arrangement, such arrangements being within the level of ordinary skill in the art.

Electronic properties that can be sensed in the systems of the invention to determine biological or chemical interaction include impedance (a combination of capacitance, inductance, and/or conductance) dielectric properties of the system (which can be derived from others of these properties listed) and the like. It is necessary only that a detectable change in electronic configuration occur. "Electronic configuration" in this context means electron transfer or other shift in electrons within a species that produces a detectable change in electronic property (such as impedance, above, creation of dipoles, and the like).

The system of FIG. 14 can operate as follows. A fluid is introduced into inlet 93 and fills container 94, exiting at outlet 95. The impedance of the system is measured, and if biological interaction between species 98 and species 104 takes place, then changes in the impedance of the system will be determined indicative of interaction of species 98 and species 104.

Figure 15:
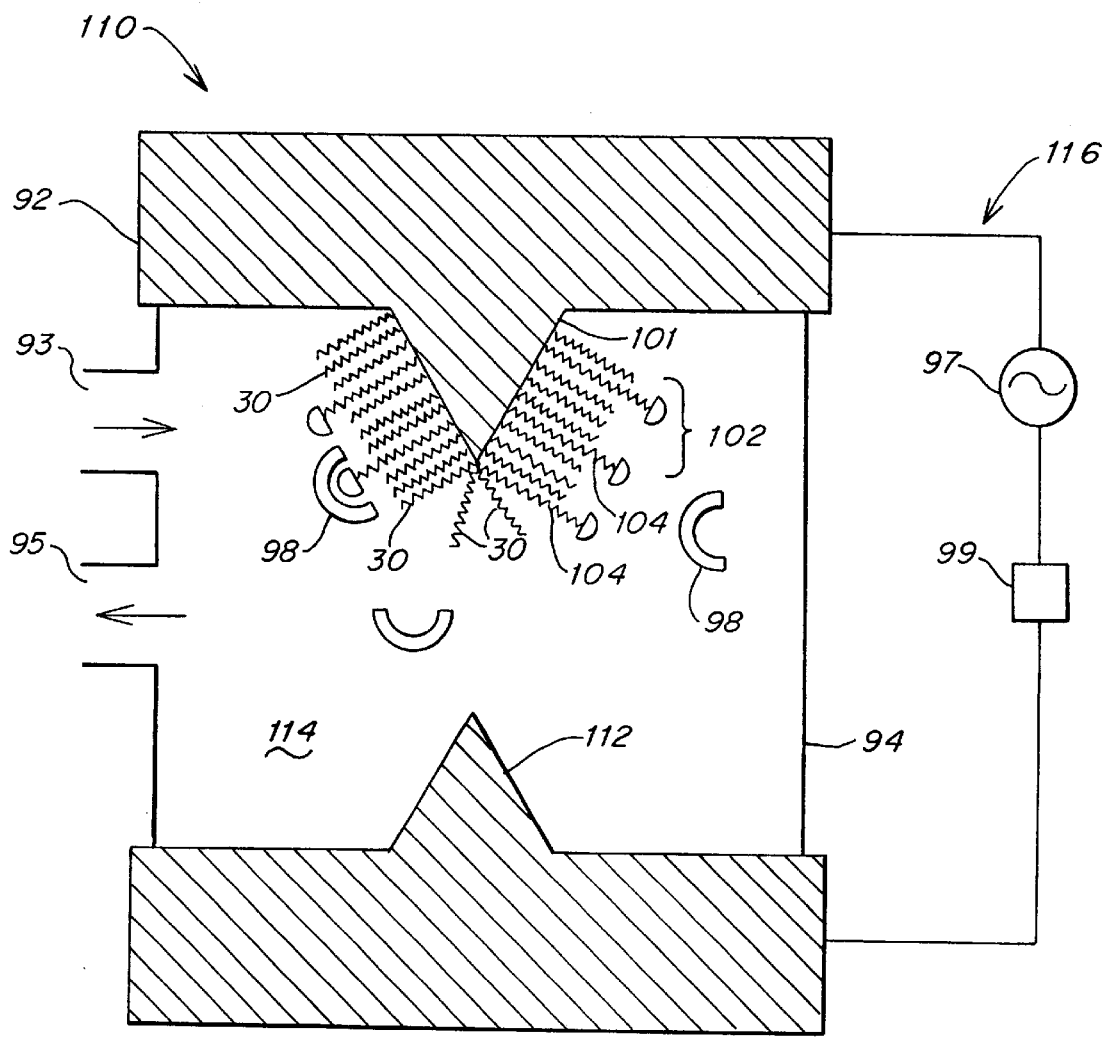
FIG. 15 is a dual-electrode electronic property probe for biological molecules.

Determination of electronic properties of molecules can be carried out using a two-electrode system as well, and such a system 110 is illustrated in FIG. 15. System 110 includes, in addition to electrode 92 and SAM 102, a second electrode 112 spaced from electrode 92. Electrode 12 can be the same as or different from electrode 92. Both electrodes can be conductive or semiconductive. The system includes a medium 114 between electrodes 92 and 112, which can be introduced into container 94 through inlet 93 and removed through outlet 95. The medium can be conductive, non-conductive, or semiconductive electrically. When medium 114 is non-conductive, the system can define a capacitor. Electrode 112 does not carry a SAM, or carries a SAM (not illustrated) made up of nonactive species, that is, species that are not chemically or biochemically active with respect to species 98. For example, a SAM of NSB-inhibiting species 30 can be provided on electrode 112 if desired.

Electrical circuit 116 is provided to electrically connect electrodes 92 and 112, and includes a source 97 of alternating current and an impedance sensor 99. In another arrangement (not illustrated) impedance is sensed by providing a source 97 or alternating current that addresses electrodes 92 and 112, a current meter in parallel with that circuit, and a voltage meter arranged, separately, across electrodes 92 and 112. This arrangement could be used also in connection with FIG. 16, described below.

The system 110 of FIG. 15 operates as follows. Species 98 is introduced into the system. If binding to species 104, or chemical or biochemical modification of species 104 occurs, then this binding is sensed by monitoring electronic changes in the real or imaging parts of impedance (including wave properties and wave echos) of the system as a function of frequency, time, and/or temperature. Electronic sensing of molecular processes also can be carried out in a two-electrode system where both electrodes present functionalized SAMs, that is, where both electrodes provide a SAM including a species that can biologically or chemically interact with a species in solution or with species of the other electrodes. This can be visualized with respect to FIG. 12, above. When the two electrodes are mechanically brought into close proximity so that interaction of the separately immobilized species occurs, the impedance of the system is changed. These changes in impedance can be detected by comparison of high frequency response profiles where changes in impedance, dielectric, or conductance as a function of frequency, time, and/or temperature are monitored. Reference can be made to Heller, "Electrical wiring of redox enzymes", ACC. Chem. Res. 23, 128–134 (1990) and Bumm, et al., "Are single molecular wires conducting?", *Science*, 271 (1996), referenced above.

The frequency range for detection associated with the system of FIG. 15 should be in the Khz to gHz frequency range. At high end frequencies impedance can be dominated by water (if present). At the low end of these frequencies, conductivity across the medium, or capacitance of the electrode itself, can dominate, preventing determination of a change in electromagnetic properties due to chemical or biochemical activity of species 98 with respect to species 104.

Figure 16:
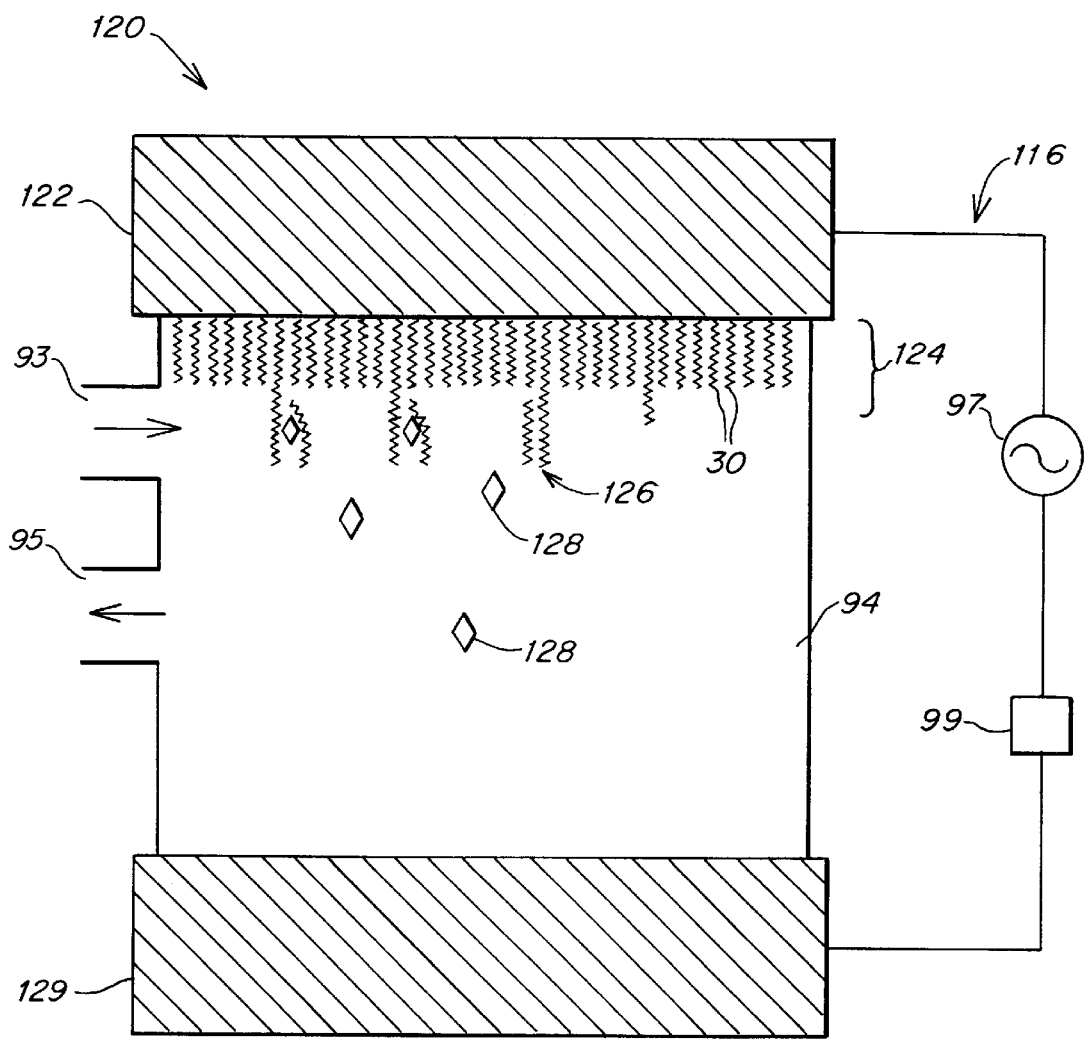
FIG. 16 is a schematic illustration of another dual-electrode electronic property probe for biological molecules.

Referring now to FIG. 16, a system 112 is illustrated schematically. System 120 is similar to system 110 with the exception that a first electrode 122 is provided including a SAM 124 defined by species 30 and, admixed with species 30, SAM-forming species 126 defining double-stranded DNA exposed at the surface. Species 128 is exposed to SAM 124 (by, for example, introduction in a fluid medium into inlet 93), and a change in chemical, biochemical, or structural characteristic of species 126 is determined. In the embodiment illustrated, species 128 (the target species) is a drug that functions in its ability to intercalate into duplex DNA (Blasko et at., "Microgonotropens and their interactions with DNA: structural characterization of the I:1 complex of D(CGCAAATTTGCG)$_2$ and Tren-microgonotropin-b by IID-NMR Spectroscopy and Restrained Molecular Modeling", *J. Am. Chem. Soc.*, 116, 3726(1994)). Species 128, which is a small molecular drug candidate, is injected into the system and changes in the structure of the system (i.e. the interruption of even one base pairing of DNA 126) cause a change in the electromagnetic properties at the surface. As the small molecular species (drug 128) intercalates into duplex DNA, the dielectric of the system is altered due to structural changes even though the molecular content of the system has not changed (Sridhar, et al., "High-frequency structural relaxation in supercooled liquids", *J. Chem. Phys.* 88, 1170 (1988)). The structural alterations (and, by implication, the action of the drug candidates) can be detected by monitoring changes in the dielectric (impedance) of the system as a function of frequency and/or time.

In another arrangement (not illustrated) a SAM on a surface of an electrode is provided. The SAM is made up of an active species, optionally (and preferably) in combination with species 30. A species is introduced, and immobilized to the active species of SAM. A second species is introduced and determination is made as to whether the second species displaces the first species coupled to the SAM-forming species. Detection can be carried out as described above involving impedance.

In another procedure, DNA hybridization and analysis of base pair mismatch (for screening genetic mutations) can be carried out. A DNA SAM is provided on an electrode, a complementary strand is exposed to immobilized DNA, and where mismatch occurs impedance or conductance is changed detectably. Determination can be made as to where in the sequence the mismatch occurs, and the identity of the mismatch, by measuring the impedance of the system as a function of frequency.

In another example, a coaxial cable defines an electrode used in a determination. The use of the known property of and modification of a coaxial cable is used. The invention, according to this embodiment, involves modification of the end of the cable with a SAM, as described above. The cable, once the end is modified, can be coupled to a network analyzer used to scan frequencies to eliminate wave reflections. Hookup of the analyzer, and comparison of the analyzer to "before" and "after" measurements (before and after exposure of the end of the cable to a medium containing a species that can chemically, biochemically, or structurally alter a species of the SAM) results in determination of the interaction. That is, wave reflection values can be compared between "before" and "after" characteristics.

As discussed, electronic sensing strategies include determination of and the modification of an immobilized species. Modification can be caused by a second species, by light, by a magnetic field, or other phenomena. One example of a chemical change is immobilization of ATP on a SAM-derivatized electrode. A catalytic substance is introduced into a conducting medium between two electrodes (for example, the arrangement as illustrated in FIG. 16). The catalyst induces change of ATP to ADP as an indicator of a biological function. This is detected by monitoring the change in impedance of the system.

Figure 17:
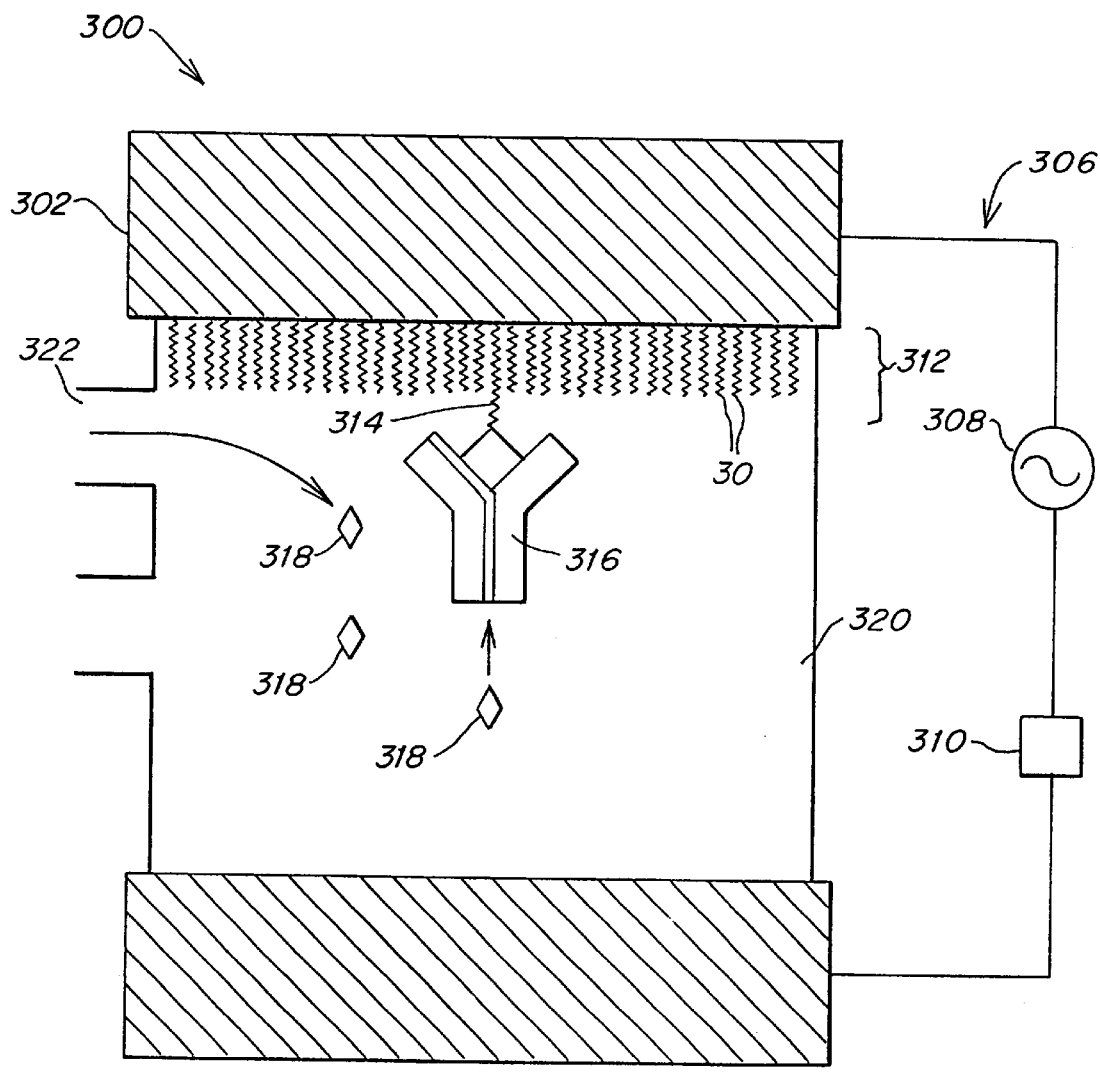
FIG. 17 is a schematic representation of yet another system for determining a change in an electronic property of a surface-immobilized molecule for drug screening.

Another aspect of the invention involves determination of a mis-folded form of a normal protein or any induced conformational change of a normal biological molecule. Determination can be made via systems such as those illustrated in FIGS. 8–16, or in connectiong with embodiments illustrated in FIGS. 17 and 18, discussed below. This embodiment can be useful in detection of changes in state of oligomerization of a biological molecule. Many disease states (including a form of breast cancer, for example) involve a receptor that is too prone to dimerization, either by overproduction of a ligand that promotes receptor dimerization or a mutation in the receptor itself. A disease state results when the dimerization state sends a constituitively "active" signal. Drugs capable of disrupting this dimerization (or, inconnection with some diseases, promoting it), could be screened in this embodiment of the invention. Referring to FIG. 17, this can be screened in device 300 including a first electrode 302, a second electrode 304, and an electrical circuit 306 connecting electrodes 302 and 304 and including a source 308 of alternating current and an impedance sensor 310. A SAM 312 includes NSB-inhibiting species 30 and an immobilized (preferably covalently via attachment to a SAM forming species) ligand 314. A receptor as a multimer 316 is immobilized at ligand 314 and a drug candidate 318 is introduced into a compartment 320 through an inlet 322. The drug candidate 318 is capable of disrupting the multimer 316. Receptors, free in solution, can be subjected to drug candidates that might promote dimerization which can result in an altered electronic characteristic (impedance) state of the system.

This invention can be used, in particular, in connection with detection of disease states involving mis-folded forms of normal proteins, e.g. transmissible prion diseases (TSE's). This includes disease states such as transmissible spongiform and encephalopathies (TSEs) such as bovine spongiform encephalopathy (mad cow disease), scrapie in sheep or in humans, Creutzefeldt-Jacob disease, fatal familial insomnia, Gerstmann-Straussler-Sheinker disease, kuru, and the like. Those of ordinary skill in the art are aware of this type of disease and what is embraced by the designation "disease states involving a mis-folded form of a normal protein". These disease states are believed to occur when a mis-folded form of a normal protein (prion) enters a mammal (see "Special News Reports Putting Prions to the Test" *Science*, 273:184–189, 1996). In a host animal, the prion is proposed to propagate a disease state by recruiting normal proteins and catalyzing the mis-folding of the normal protein so that the normal protein, in turn, goes on to infect other normal cells and tissues of the host mammal. A longstanding problem in the art is the inability to effectively detect disease states involving mis-folding of normal proteins. Typically, in the prior art, disease states of these types can be detected only in a late stage of the disease. The disease typically is first detected clinically by behavioral changes in a mammal, and is verified after death of the mammal by visual inspection of defects in the brain (sponge-ike holes). However, earlier detection of this type of disease state would be extremely beneficial since the prion is very resistant to protease and heat treatment, and remains infectious unless treated with harsh organic solvents. Because of the great risk of transmission to humans or other mammals from tainted meat or feed (even if cooked) preclinical diagnosis has become a significant area of research, although prior to the present invention, simple and reliable preclinical diagnosis has not resulted. The present invention provides simple, pre-clinical diagnosis involving obtaining a fluid sample of a mammal e.g., blood, tears, a non-invasive tissue sample such as a needle biopsy of a tonsil, tissue homogenates, and the like, and subjecting the sample to a test to determine the presence of prion.

Referring to FIG. 16, this can be envisioned by use of system 120 where SAM 124 includes NSB-resistant component 30 in combination with a SAM-forming species analogous to species 126 but to which normal protein is immobilized covalently, or via the polyamino acid tag/chelate arrangement described above, or the like. Alternatively, the entire SAM can be made up of immobilized protein, but it is preferred that the SAM included NSB-resistant species 30 present according to proportions described above. Exposure of this system (through inlet 93 to a fluid sample containing a fluid or tissue sample of a mammal suspected of containing a TSE disease state, if the disease state is present, it will result in mis-folding of the normal protein immobilized at the surface via the SAM, resulting in a change in the electronic configuration of the immobilized protein indicated by a detectible change in electrical properties of the system, such as a change in impedance of the system (capacitance). The change in conformation of the immobilized protein induced by the prion or associated cofactor (which is indicative of the disease state) is detectible. Prior studies have been conducted involving determining a change in material conformation of a molecular species via a detectible change in capacitance between a capacitor. Specifically, glass in a liquid state and in a solid state, in a capacitor, has been studied and the change between liquid and solid has been detected via a change in capacitance. This change in electrical property is due to a change in material confirmation alone. The Applicant is not aware of prior studies that have taught or suggested application of this technique to biological systems.

This aspect of the invention is particularly useful since it makes otherwise very difficult detection of a change in conformation of a biological molecule possible. Prion detection has been difficult in the past because the amino acid sequence of the normal and the mis-folded proteins are identical. The normal protein has been proposed to be predominantly an a-helical while the prion form is a β-sheet. Early detection is very important in live stock since, for example, scrapie has an incubation period of about two years before presentation of clinical systems and, in the interim, great expense to raise the animal is wasted.

Changes in capacitance due to liquid/solid change in glass is described by Sridhar et al., "High Frequency Structural Relaxation in Supercooled Liquids" *J. Chem. Phys.* 88, 1170–1176 (1988).

In another aspect the invention involves a spacially-addressable surface array of biological molecules, i.e., a "combinatorial" array in which each individual region of the array is individually addressable electronically, and each can serve to detect, via determination of a change in electronic property of a surface-immobilized species, a chemical or biochemical interaction at that surface. This can be envisioned with reference to FIG. 13 in combination with FIG. 16. An array as illustrated in FIG. 13, created via micro contact printing, via formation of a thin film of metal such as gold on a surface followed by scoring of the surface to electronically isolate individual regions of the film, or the like can be provided. Each individual, isolated metal region serves as an electrode and is individually addressable, for example through the substrate. In another embodiment, photo lithographic techniques or micro contact printing in combination with plating or etching can result in an array of individually-addressable electrodes each addressed by a lead on the top surface 68 of electrode 66 of FIG. 13. Electrode 66 of FIG. 13, in combination with an electrode such as electrode 124 of FIG. 16 (that can be free of any SAM) can be provided in combination, or the electrode carrying the combinatorial array can be provided alone as in FIG. 14. The use of combinatorial arrays is known (see "Special Report: Combinatorial Chemistry" *Chemical & Engineering News*, Feb. 12, 1996, page 28+). In the invention, individual chemical or biochemical species are provided at individual, isolated electrode regions of the array, the array is exposed to a medium suspected of containing a species that interacts with at least one immobilized chemical or biochemical species, and a change in electronic property of a surface-immobilized species indicates interaction at the relevant electrode of the array, identifying the surface-immobilized species involved in the reaction, thus identifying the species to which the surface was exposed. Essentially any chemical or biochemical interaction can be determined in this manner, for example mass screening of drugs, and the like.

One advantage of this system is that the determination is not only qualitative, but quantitative. That is, not only can interaction of a species immobilized at the surface with a species to which the surface is exposed be detected, but the degree of interaction scales with the degree of change of electronic property at the surface, thus the degree of interaction can be determined, not just the existence of the interaction.

This aspect of the invention is a significant improvement over the state of art as known to the applicant in which random sequences of peptides are synthesized on beads, on a spacially addressable surface (such as combinatorial array) or displayed by phage. Target proteins are tagged with a visual marker (usually a fluorescent tag) and the beads or surfaces are incubated with the target molecule to allow for binding. After several washing steps, beads that fluoresce are isolated or the positions on the surface that fluoresce are identified. The sequence of a peptide in a spacially addressable array that interacts with the target molecule is determined, in the prior art, by a photo-masking scheme. The sequence of peptides on beads that interact is identified by micro-sequencing techniques. One drawback of the prior art techniques is that, in affinity studies of small peptides, degradation in the body, diversity, and representation are problematic. If a peptide in a study is provided as an 8-mer (eight peptide units) the peptide is not large enough to provide the structure necessary for accurate binding determination. On the other hand, if a larger peptide (e.g., a 20-mer) is used, better structural integrity exists and a better chance of binding exists. However, this option involves under-representation since one would need approximately $10^{25}$ different peptides for all possibilities to be screened. It is not feasible to make and screen random 20-mers and barely feasible for 10-mers. The usual length of a randomly synthesized peptide is an 8-mer which, in many cases, is unacceptable conformationally. Additionally, a peptide that is small enough to be readily synthesized and screened typically is degraded by the mammalian body too quickly to compete with native proteins.

Figure 18:
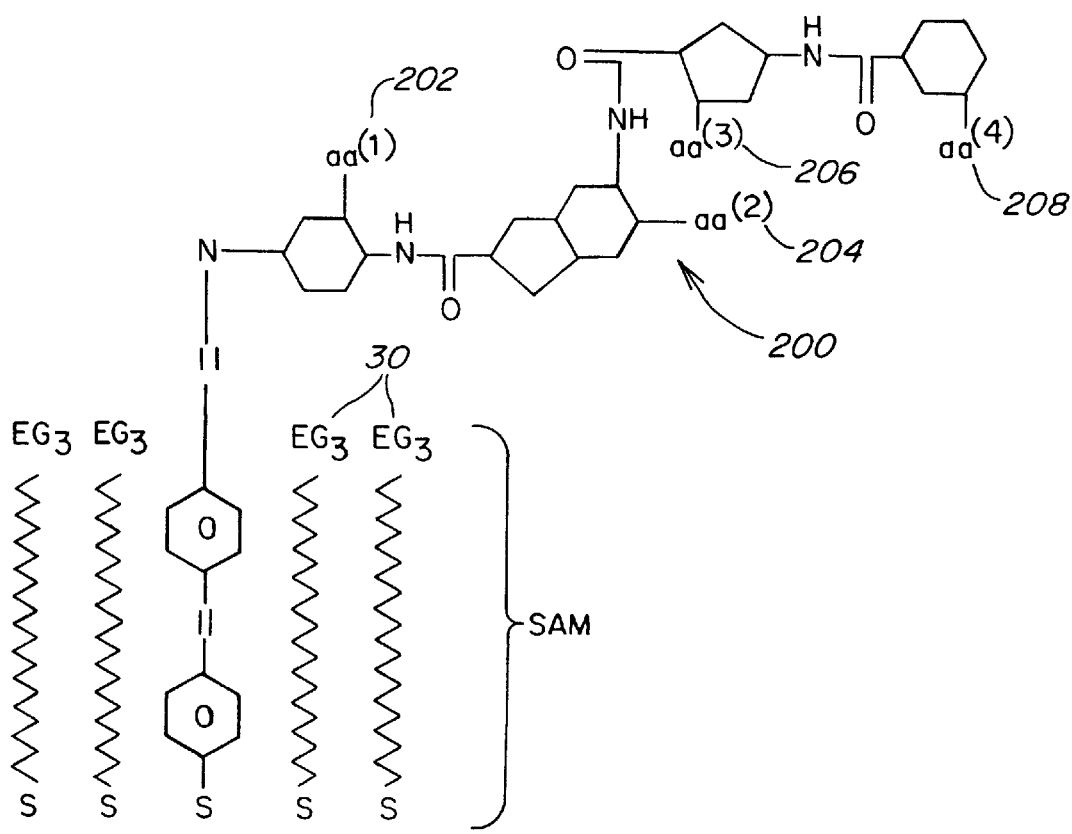
FIG. 18 is a schematic representation of a cyclic backbone structure providing covalent surface immobilization for attached molecules as part of a SAM.

The present invention solves this problem by using cyclic compounds, currently studied as denovo structural elements, but not, according to the applicant's knowledge, for drug discovery, in an inter-connected linkage defining an unnatural polymer. The technique involves, by a photosynthetic and photo-masking technique, synthesizing a spacially addressable surface array (FIG. 13) of a SAM including, at each individual array location, an immobilized putative binding partner 200, as illustrated in FIG. 18. Species 200 includes amino acids 202, 204, 206 and 208, linked to cyclic structures. Cyclic structures of this general type have been described by Gellman and Kiessling, albeit without any teaching or suggestion of attaching functionalities to them. Each individual molecule 200 is different, and is provided at a location of the combinatorial array. The surface is incubated with a putative binding partner, then washed. The added mass of molecules that interact with the surface cause changes in the electronic properties of the system. The spacial location of the surface-immobilized species that interact with the target molecule can be identified electronically since the sequence of the immobilized species is pre-determined by a masking scheme; its physical location in the array identifies the sequence.

Species 200 (FIG. 18) also can be an oligonucleotide such as DNA including unnatural bases derivatized with functionalities for the acceptance of modifying molecules (bases available from Glenn Research). The amino acids can be attached to these bases. In this case the oligonucleotide provides the structure, and the amino acids provide specificity.

This system also can be applied to beads or other supports and incubation can take place with a fluorescently-tagged target protein. Binding candidates can be visualized and then isolated.

The immobilized species to be synthesized can be a simple peptide or nucleic acid. Alternatively, it can be a polymer of ring compounds connected by amide bonds, as illustrated in FIG. 18, or pseudo peptide bonds such as a vinylogous backbone (Gellman, *Nature*, August 1996). Gellman describes ring compounds connected by amide bonds that are protease resistant and also form repetitive tertiary structures. The cyclic polymers can be synthesized in much the same way as a peptide. The rings can easily be modified with a functionality to accommodate the attachment of an amino acid. The resultant pseudo peptide gains rigidity from the ringed structures and specificity from the amino acid. A rigid scaffold for the presentation of amino acids simplifies the diversity and representation problem. If the rigidity from three amino acids can be replaced by one ring compound then the synthesis problem is simplified by a factor of 8,000. In this case, a 20-mer can be represented by four ring compounds plus eight amino acids. Five amino acids that contribute to structure can be eliminated.

DNA-containing SAMs can be used for the identification of randomly-sequences peptides (natural or unnatural) or small molecule polymers. Random synthesis of peptides or small molecule polymers can be carried out on beads or on other supports and each synthetic step tagged by a four-digit DNA code. Drug candidate beads can be incubated with a tagged target protein. The sequence of an interacting species can be identified by passing the bead over a DNA-SAM array. The code and thus the sequence of the polymer is identified by visualization or electronic detection of hybridization to the complementary DNA presented by the SAM.

The function and advantage of these and other embodiments of the present invention will be more fully understood from the examples below. The following examples are intended to illustrate the benefits of the present invention, but do not exemplify the fill scope of the invention. References cited in the following examples are incorporated herein by reference for all purposes.

EXAMPLE 1

Preparation of Nitrilotriacetic Acid Chelate Linked Via Spacer Moiety to Thiol

Undec-1-en-11-yl tri(ethyleneglycol) (1) was synthesized according to a procedure reported by Pale-Grosdemange, C.;

Simon, E. S.; Prime, K. L; Whitesides, G. M. *Journal of the American Chemical Society*, 113, 12, (1991).

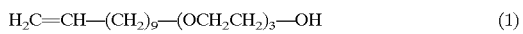
$$H_2C=CH-(CH_2)_9-(OCH_2CH_2)_3-OH \quad (1)$$

N-(5-amino-1-carboxypentyl)iminodiacetic acid (2) was synthesized according to a procedure reported by Hochuli, E.; Dobeli, H.; Schacher, a. *Journal of Chromatography*, 411, 177 (1987).

$$H_2N-(CH_2)_4-CH(CO_2H)(N(CH_2CO_2H)_2) \quad (2)$$

Carbonyldiimidizole (2.3 g, 2 eq. was added to a stirring solution of 2.2 g of alcohol (1) dissolved in 25 ml methylene chloride. After stirring for 2 hours, the solution was applied to a 300 g column of silica equilibrated with ethyl acetate and the imidazole carbamate eluted with 1 liter of ethyl acetate. Evaporation of the solvent under reduced pressure gave 2.7 g (95%) of the imidazole carbamate as an oil.

Amine (2) (5.0 g) was dissolved in 100 ml of water. The pH was titrated to 10.2 with 12 N NaOH, then 130 ml of dimethylformamide was added. The imidazole carbamate (2.5 g in 10 ml dimethylformamide) then was added dropwise to aqueous solution of (2) while stirring. After 12 hours, the solution was added to 500 ml water and washed three times with ethyl acetate by gently stirring to avoid the formation of an emulsion. The aqueous phase then was acidified with 6 N HCl to pH 1.5 and extracted into ethyl acetate (4×250 ml). The combined extracts were washed with saturated NaCl, dried over $MgSO_4$, and the solvent removed under reduced pressure to give 1.8 g (50%) of olefin (3) as a hydroscopic white solid.

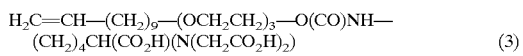
$$H_2C=CH-(CH_2)_9-(OCH_2CH_2)_3-O(CO)NH-$$
$$(CH_2)_4CH(CO_2H)(N(CH_2CO_2H)_2) \quad (3)$$

To olefin (3) (1.7 g) dissolved in 15 ml distilled tetrahydrofuiran was added 0.5 ml thiolacetic acid and 100 mg 2,2'-azobis(2-methylpropionitrile) (AIBN). The solution was irradiated for four hours under a 450 W medium pressure mercury lamp (Ace Glass). The solvent was removed under reduced pressure and the crude product triturated with hexane. Recrystalization from ethyl acetate/hexane gave 1.8 g (94%) of thioacetate as a hydroscopic tan solid (4).

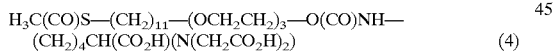
$$H_3C(CO)S-(CH_2)_{11}-(OCH_2CH_2)_3-O(CO)NH-$$
$$(CH_2)_4CH(CO_2H)(N(CH_2CO_2H)_2) \quad (4)$$

To thioacetate (4) (0.67 g) in 20 ml dimethoxyethane was added 17 ml water, then 20 mg $I_2$. After the addition of 3 ml of 2 N NaOH, the solution was stirred for four hours while bubbling with $O_2$. Addition of 100 ml of water and acidification to pH 1.5 with 6N HCl lead to precipitation of the product as the disulfide. The disulfide was filtered, washed with water and dried under vacuum to give 0.55 g (89%) of a white powder.

The disulfide was reduced to the thiol (6) with triethylphosphine. To the disulfide (0.42 g) in 18 ml methanol plus 2 ml water under an atmosphere of nitrogen, was added 0.3 g of triethylphosphine. The solution was stirred for five hours then concentrated to an oil under reduced pressure. The residue was dissolved in 30 ml degassed water and acidified to pH 1.5 with 6N HCl. The product was extracted three times with 20 ml ethyl acetate. The combined organic phases were washed with saturated NaCl, dried over $MgSO_4$, and concentrated under reduced pressure to thiol-linked nitrilotriacetic acid chelate (5) as a tan hydroscopic solid (0.24 g, 57%).

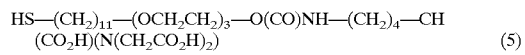
$$HS-(CH_2)_{11}-(OCH_2CH_2)_3-O(CO)NH-(CH_2)_4-CH$$
$$(CO_2H)(N(CH_2CO_2H)_2) \quad (5)$$

EXAMPLE 2

Preparation of SPR Chip Derivatized with Self-Assembled Mixed Monolayer of Chelate and Nonspecific Binding Inhibitor 11-mercaptoundec-1yl oligo(ethyleneglycol) (6) was synthesized according to a procedure reported by Pale-Grosdemange, et al., *JACS* (1991; above).

$$HS-(CH_2)_{11}-(OCH_2CH_2)_n-OH \quad (6)$$

The gold surface of an SPR chip from Pharmacia Biosensor, Piscataway, N.J. was cleaned using 70:30 $H_2SO_4/H_2O_2$ to remove all species on the gold. 11-mercaptoundec-1yl oligo(ethyleneglycol) (6) and the thiol-linked nitrilotriacetic acid chelate (5) described in example 1 were dissolved in ethanol in a 95:5 molar ratio, at a total concentration of 1 mM. The chip surface was exposed to the 1mM solution of the thiols in ethanol for 24 hours, then washed with 955 ethanol and allowed to dry. The derivatized surface was characterized by X-ray photoelectron spectroscopy, which revealed that a mixed monolayer had adhered to the surface, the mixed monolayer including a ratio of (6) and (5) approximately equal to the concentration of those species in the solution from which the surface was derivatized (95:5 molar ratio of (6) to (5)).

EXAMPLE 3

Incorporation of Metal Cation into Chelate of SelfAssembled Monolayer on SPR Chip The surface derivatized as described in example 2 to have adhered a self-assembled mixed monolayer formed of a 95:5 molar ratio of species (6) and (5) was further modified to allow the chelate to coordinate nickel dication ($Ni^{2+}$). The mixed monolayer was washed with 1 mM aqueous NaOH followed by 1% aqueous $Ni(SO_4).6H_2O$, resulting in species (5) coordinating $Ni^{2+}$ to define species (7).

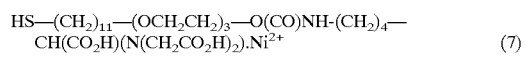
$$HS-(CH_2)_{11}-(OCH_2CH_2)_3-O(CO)NH-(CH_2)_4-$$
$$CH(CO_2H)(N(CH_2CO_2H)_2).Ni^{2+} \quad (7)$$

EXAMPLE 4

Coordination of Biological Binding Partner to Metal Cation

Gal 11 has been identified as a protein required for efficient galactose utilization in yeast. Nogi, Y.; Fukasawa, T. *Curr. Genet.* 2, 115–120 (1980). Gal 11 p (potentiator) is a 44 kD mutant of Gal 11, differing from Gal 11 at a single amino acid only Id. Gal 11 is a suspected biological binding partner of Gal 4 (see discussion in example 5). A "mini" form of Gal 11 p was expressed and purified (residues 261–351+799–1081) with a polyamino acid tag at a location remote from the recognition region of the protein fragment. Specifically, a run of six histidines is expressed at the amino terminus of the protein fragment, and the histidine-tagged Gal 11 p was isolated out of cell extracts by absorption on a column containing nickel dication coordinated to a nitrilotriacetic acid derivative. Hochuli, et al. *J. Chromatog.* 411, 177 (1987), Gentz, R.; Chen, C.; Rosen, C. A.; *Proc. Natl. Acad. Sci.* 86, 821 (1989).

The polyamino acid-tagged binding partner was attached selectively to the derivatized surface described in example 3 by coordination to the metal cation via the histidine tag. specifically, a 0.25 mg/ml aqueous solution of Gal 11 p was injected into a delivery channel of a BIAcore™ SPR instrument, Pharmacia Biosensor. The result was a surface carrying a plurality of binding partners (Gal 11 p) oriented such that a substantial portion of the recognition regions for Gal 4 face away from the chip surface and are readily available for biological binding with the biological molecule Gal 4.

EXAMPLE 5

SPR Determination of Gal 4 Using Chip Derivatized with Self-Assembled Monolayer of Alkyl Thiol Terminating in Metal Chelate Coordinated by Polyamino Acid-Tagged Gal 11 p This example examines the sensitivity of the SPR technique for the analysis of the interaction between biological binding partners, with use of an SPR chip prepared in accordance with the present invention. Specifically, the interaction between the transcription promoter Gal 4 and Gal 11 p (which contains increased area of hydrophobicity relative to Gal 11), was studied, using a BIAcore™ SPR instrument available from Pharmacia Biosensor, Piscataway, N.J.

It has been reported that in cells deleted for Gal 11, activation by Gal 4 is reduced some 5–20 fold, an effect that can not be accounted for by decreased levels of the activator. Id, Himmelfarb, H. J.; Pearlberg, J.; Last, D. H.; Ptashne, M. Cell 63, 1299–1309 (1990), Suzuki, Y.; Nogi, Y.; Abe, a.; Fukasawa, T. *Molecular and Cell Biology* 8, 4991–4999 (1988), Long, R. M.; Mylin, L. M.; Hopper, J. E. *Molecular and Cell Bioloy* 11, 2311–2314 (1991). It is suspected that proteins containing the Gal 4 region that recognizes Gal 11 p in vivo interact in vitro with Gal 11 p but not with Gal 11 (wild type).

It is also suspected that Gal 4 promotes transcription by facilitating the necessary proximity of a holoenzyme containing Gal 11 with the TATA box on DNA. It has been reported that Gal 4, truncated to completely abolish its activating domain, is transcriptionally active in the presence of the holoenzyme containing Gal 11 p (but not in the presence of the holoenzyme containing Gal 11). Accordingly, it has been postulated that Gal 11 p interacts hydrophobically with truncated Gal 4 to facilitate transcription.

SPR was used to study the interaction of Gal 4 with the immobilized his-tagged Gal 11 p. It was observed that Gal 11 p binds Gal 4, but does not bind a number of other transcription promoters. Histidine-tagged wild-type Gal 11, immobilized on the SPR chip in the same manner, did not bind Gal 4. None of the transcription promoters demonstrate NSB on the mixed monolayer. That is, in the absence of Gal 11 p immobilized on the surface, no transcription promoters bound to the surface, and in the presence of immobilized Gal 11 p, only Gal 4 was bound.

The interaction between Gal 11 p and Gal 4 was not observed by co-immunoprecipitation or on an affinity column, demonstrating the importance of the orientation in the presentation of the protein to the analyte solution, achievable in accordance with the present invention.

EXAMPLE 6

Comparative Attempted SPR Determination of SRB2 Using Standard Dextran Chip Carrying Gal 11

This example examines the sensitivity of the current state-of-the-art SPR chip, which comprises a layer of dextran on the gold SPR chip surface.

In this example, an attempt was made to study the interaction of Gal 11 (wild-type) and the RNA polymerase B suppressor SRB2, a 28 kD member of the holoenzyme described in example 5 (the multi protein complex which assembles on the DNA at the TATA box and with which a DNA-bound activator must interact in order to activate transcription). Koleske, a. J.; Young, R. A. *Nature*, 368, 466–469 (1994). As discussed in example 5, Gal 11 p interacts with Gal 4, thus it is important to find a target of Gal 11 on the holoenzyme. Detection of this type of interaction is difficult because transcription factors generally exhibit low affinity for their targets, such that positive control of transcription of achieved only through the correct assembly of several factors. The 30 kD protein SRB5 was used as a negative control in this example. SRB5 is shown by genetic experiments not to interact with Gal 11 or Gal 11 p Id.

An SPR chip having a layer of dextran on gold (#BR1000-14) was purchased from Pharmacia Biosensor., and the SPR instrument described above was employed.

FIG. 1 illustrates a sensorgram plotting resonance units (RU) as a function of time associated with this example. The flow rate of sample across the chip surface was 5 ul/min. The sensorgram of FIG. 1 is labeled with reference numerals that correspond to the steps of the experimental protocol below.

1. (t=240 sec) description of chip type; standard dextran
2. (t=731 sec) end of injection of EDC/NHS which activates the carboxylates on the dextran surface.
3. (t=1326 sec) end of injection of 35 ul wild type Gal 11 at 0.025 mg/ml, in NaOAc buffer at pH 4.5.
4. (t=1440 sec) preinjection baseline
5. (t=1928 sec) end of injection of ethanolamine, which blocks the activated carboxylates that did not covalently link to a protein.
6. (t=2179 sec) preinjection baseline
7. (t=2668 sec) end of injection of SRB2 at 0.25 mg/ml diluted with the running buffer PBS.
8. (t=2991 sec) preinjection baseline
9. (t=3472 sec) end of injection of SRB2 at 0.5 mg/ml
10. (t=3639 sec) preinjection baseline
11. (t=4122 sec) end of injection of SRB5 at 0.25 mg/ml
12. (t=4218 sec) preinjection baseline
13. (t=4814 sec) end of injection of SRB5 at 0.5 mg/ml
14. (t=5610 sec) preinjection baseline
15. (t=6128 sec) end of injection of myc-a, a monoclonal antibody which should bind to Gal 11, at 0.25 mg/ml.

Tabulated below are protein absorption response values (AbsResp; RU units) and response values relative to preceding baseline (RelResp; RU units) corresponding to the protocol steps above.

|     | Time    | AbsResp | RelResp |
| --- | ------- | ------- | ------- |
| 1.  | 240.00  | 9150    |         |
| 2.  | 731.00  | 9313    |         |
| 3.  | 1326.50 | 13444   | 4131    |
| 4.  | 1440.00 | 13291   | 3978    |
| 5.  | 1928.00 | 12950   | 3637    |
| 6.  | 2179.00 | 12872   | 3559    |
| 7.  | 2668.00 | 12923   | 51      |
| 8.  | 2991.00 | 12880   | 8       |
| 9.  | 3472.00 | 12976   | 96      |
| 10. | 3639.00 | 12895   | 15      |

-continued

| | Time | AbsResp | RelResp |
|---|---|---|---|
| 11. | 4122.00 | 12911 | 17 |
| 12. | 4218.00 | 12887 | −8 |
| 13. | 4814.00 | 12941 | 54 |
| 14. | 5610.00 | 12852 | −35 |
| 15. | 6128.00 | 12940 | 87 |

4131 RUs of Gal 11 bound to the dextran. The interaction of Gal 11 with SRB2 yielded an absorption of 51 RU's at [SRB2]=0.25 mg/ml; at [SRB2]=0.50 mg/ml, the absorption was 96 RUs. By contrast, at [SRB5]=0.25 mg/ml the absorption was 17 RU's, while at [SRB5]=0.5 mg/ml, the absorption was 54 RUs. Lastly, at [myc-a]=0.25 mg/ml, the absorption was 87 RU's.

Since the negative and positive controls (SRB5 and myc-a, respectfully) gave essentially the same results, no conclusions regarding binding can be reached. This example demonstrates that the current state-of-the-art dextran chip does not provide the sensitivity necessary for determination of biological binding between Gal 11 and SRB2.

EXAMPLE 7

SPR Determination of SRB2 Using Chip Derivatized with Self-Assembled Monolayer of Alkyl Thiol Terminating in Metal Chelate Coordinated by Polyamino Acid-Tagged Gal 11

As in example 5, this example demonstrates the sensitivity of the SPR technique using a chip derivatized in accordance with the present invention. An SPR chip prepared in accordance with example 2 was mounted in the instrument, modification of the chip to chelate nickel dication was effected in accordance with example 3, the modified chip surface was exposed to histidine-tagged Gal 11, and SPR response to introduction to the chip surface of SRB2 and SRB5 was investigated.

Figure 2:
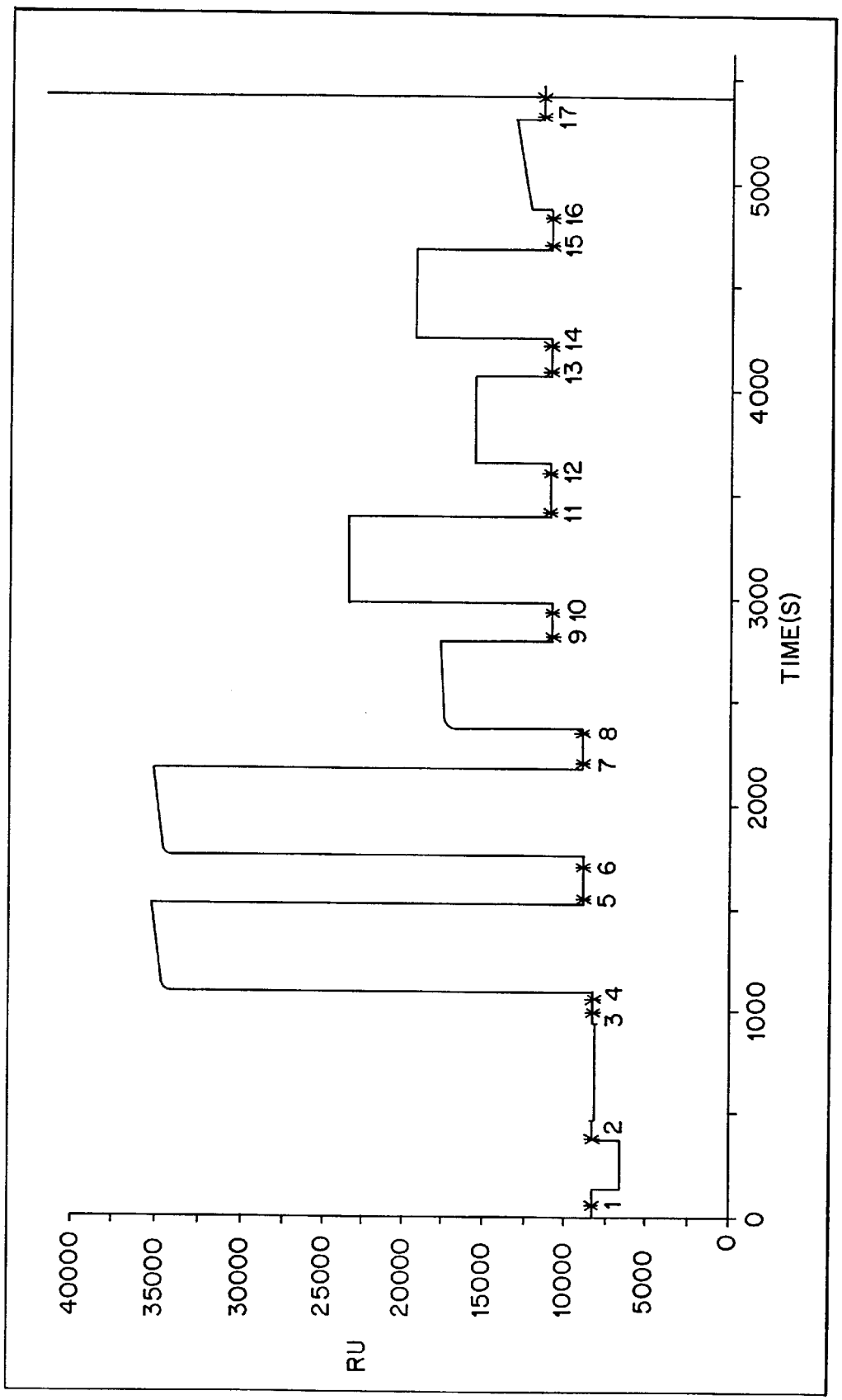
FIG. 2 is a SPR sensorgram illustrating response of a chip derivatized in accordance with the present invention, and carrying Gal 11, to SRB2.

FIG. 2 illustrates a sensorgram plotting resonance units as a function of time associated with this example. The flow rate of sample across the chip surface was 5 ul/min. The sensorgram of FIG. 2 is labeled with reference numerals that correspond to the steps of the experimental protocol below.

1. (t=50 s) chip description; 5% Ni ligand
2. (t=390 s) end of injection of 1 mM NaOH
3. (t=993 s) end of injection of 1% NiSO$_4$
4. (t=1055 s) preinjection baseline
5. (t=1555 s) end of injection of Gal 11 at 0.025 mg/ml
6. (t=1703 s) preinjection baseline
7. (t=2222 s) end of injection of a second Gal 11 injection at the same concentration to achieve maximum chip coverage.
8. (t=2343 s) preinjection baseline
9. (t=2821 s) end of injection of SRB2 at 0.25 mg/ml
10. (t=2932 s)preinjection baseline
11. (t=3438 s) end of injection of SRB2 at 0.5 mg/ml
12. (t=3610 s) preinjection baseline
13. (t=4116 s) end of injection of SRB5 at 0.25 mg/ml
14. (t=4238 s) preinjection baseline
15. (t=4728 s) end of injection of SRB5 at 0.5 mg/ml
16. (t=4842 s) preinjection baseline
17. (t=5330 s) end of injection of myc-a at 0.25 mg/ml Tabulated below are protein absorption response values (AbsResp; RU units) and response values relative to preceding baseline (RelResp; RU units) corresponding to the protocol steps above.

| | Time | AbsResp | RelResp |
|---|---|---|---|
| 1. | 50.50 | 8297 | |
| 2. | 390.00 | 8258 | |
| 3. | 993.00 | 8374 | |
| 4. | 1055.00 | 8368 | 0 |
| 5. | 1555.50 | 9122 | 753 |
| 6. | 1703.00 | 8887 | 519 |
| 7. | 2222.00 | 9197 | 828 |
| 8. | 2343.00 | 9042 | 673 |
| 9. | 2821.00 | 10998 | 1956 |
| 10. | 2932.00 | 10927 | 1885 |
| 11. | 3438.00 | 11174 | 2132 |
| 12. | 3610.00 | 11090 | 2048 |
| 13. | 4116.00 | 11138 | 47 |
| 14. | 4238.00 | 11100 | 10 |
| 15. | 4728.00 | 11174 | 73 |
| 16. | 4842.00 | 11129 | 28 |
| 17. | 5330.00 | 11578 | 450 |

In contrast to the prior art embodiment examined in example 6, substantial binding of SRB2 to immobilized Gal 11 was observed. Importantly, no nonspecific binding of SRB5 to Gal 11 was observed. Specifically, 673 RUs of histidine-tagged Gal 11 bound to the surface exposing chelate coordinating nickel dication. The interaction of Gal 11 with SRB2 yielded an absorption of 1956 RUs at [SRB2]=0.25 mg/ml; at [SRB2]=0.50 mg/ml, the absorption increased by an additional 176 RU's, for a total of 2132 RU's of bound protein. By contrast, at [SRB5]=0.25 mg/ml the absorption was 47 RUs, while at [SRB5]=0.5 mg/ml, the absorption was 73 RUs. Lastly, at [myc-a]=0.25 mg/ml, the absorption was 450 RU's. These results clearly show that the biological molecule SRB2 bound to its binding partner Gal 11. The negative control SRB5 did not bind, and the positive control myc-a did bind.

As additional control experiments: (1) SRB2 was brought into contact with a chip incorporating a metal ion (prepared in accordance with example 3) that did not have coordinated to it a the binding partner Gal 11, and (2) SRB5 was flowed over the chip after coordination of Gal 11 prior to the introduction of SRB2. No significant binding was observed in either case.

This experiment demonstrates that a biosensor surface prepared in accordance with the present invention, which provides biological binding partners oriented to stably expose recognition regions to an analyte solution, is superior to the prior art surface.

EXAMPLE 8

Comparative Attempted SPR Determination of Monoclonal Antibodies Using Standard Dextran Chip Carrying T Cell Receptor As in example 5, this example examines the sensitivity of the current state-of-the-art SPR chip, which comprises a layer of dextran on the gold SPR chip surface.

In this example, an attempt was made to study the interaction of a soluble 42 kD chimeric T cell receptor (TCR), herein referred to as ABC, with 2 monoclonal antibodies of MW=155 kD (C1 and βF1). C1 recognizes a conformational epitope thought to be near the active site of the receptor, while βF1 recognizes a linear epitope of the constant domain. Although the structure of a TCR has not yet been solved, by analogy to IG structure, the C1 epitope should reside near the "top" of the protein and the βF1 epitope near the "bottom", where the bottom is defined as the histidine tag of the protein. Probing the TCR with C1 demonstrated the availability of a defined site on the protein. The ratio of C1:βF1 binding is the ratio of correctly:incorrectly folded protein, since C1 was shown to occlude the binding site of βF1 when the TCR is bound to a surface (data not shown).

Figure 3:
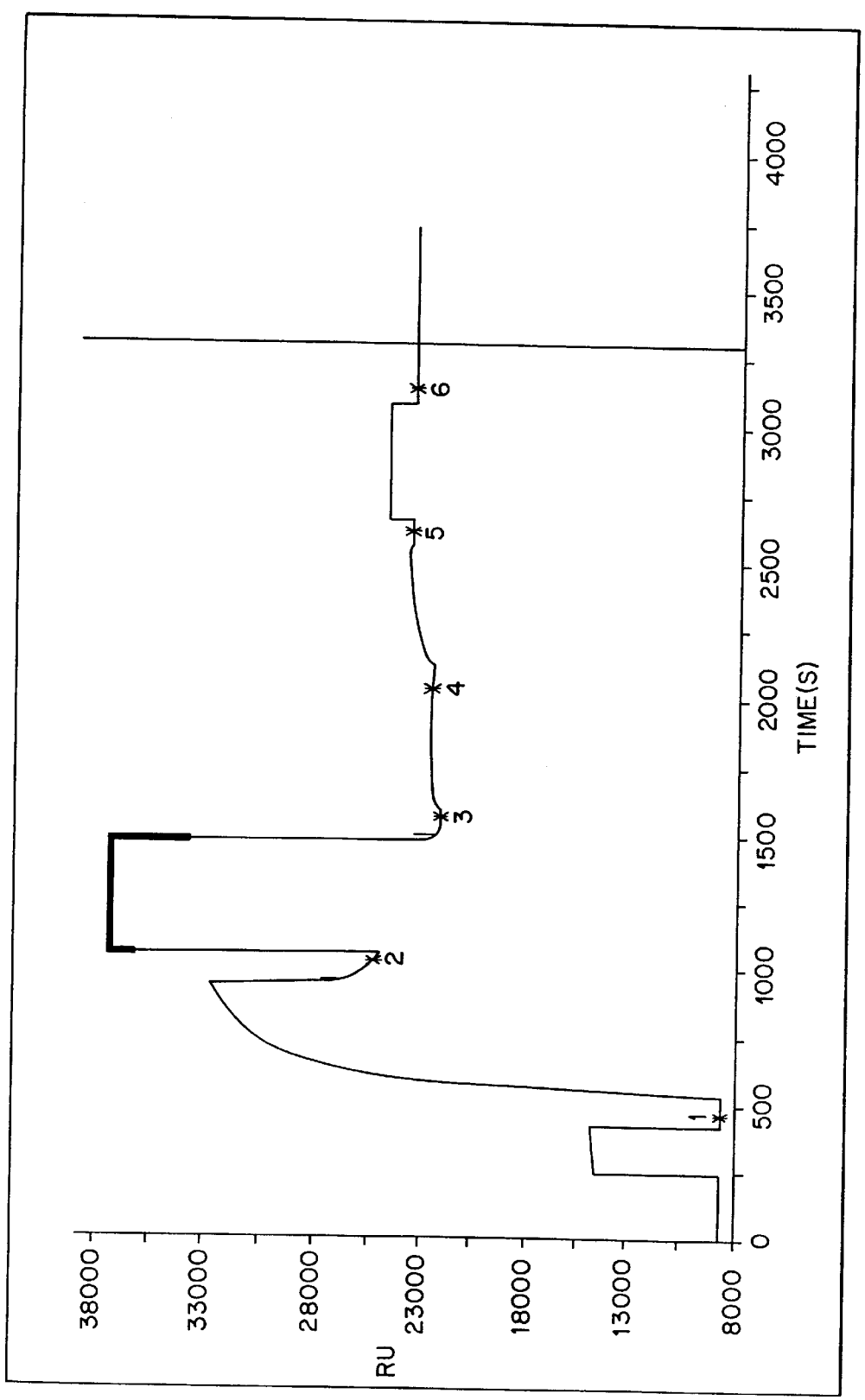
FIG. 3 is a SPR sensorgram illustrating response of a prior art chip carrying a T cell receptor (ABC) to monoclonal antibodies C1 and BF1.

FIG. 3 illustrates a sensotgram plotting resonance units as a function of time associated with this example. The flow rate of sample across the chip surface was 5 ul/min. The sensorgram of FIG. 3 is labeled with reference numerals that correspond to the steps of the experimental protocol below.

1. (t=470 s) end of injection of EDC/NHS
2. (t=1044 s) end of injection of ABC at 0.125 mg/ml in PBS buffer
3. (t=1579 s) end of injection of ethanolamine
4. (t=2047 s) end of injection of C1 at 0.2 mg/ml in PBS
5. (t=2630 s) end of injection of βF1 at 0.2 mg/ml in PBS
6. (t=3152 s) end of injection of myc-a. at 0.2 mg/ml in PBS Tabulated below are protein absorption response values (AbsResp; RU units) and response values relative to preceding baseline (RelResp; RU units) corresponding to the protocol steps above.

|     | Time    | AbsResp | RelResp |
|-----|---------|---------|---------|
| 1.  | 470.50  | 8717    |         |
| 2.  | 1044.00 | 25276   | 16558   |
| 3.  | 1579.00 | 22216   | 13499   |
| 4.  | 2047.00 | 22675   | 459     |
| 5.  | 2630.00 | 23728   | 1512    |
| 6.  | 3152.00 | 23658   | 1442    |

13,499 RU's of ABC bound to the dextran surface. The interaction with C1 led to an absorption increase of 459 RUs, while that with βF1 led to an additional 1053 RU's. Finally, the myc-a antibody did not bind. The ratio of C1:ABC was 1:29. The ratio of C1:B1 was 1:2.3. Since the molecular weight of C1 is 3.7 times that of ABC, the molar ratio of C1:ABC is 1:108, which implies that only 0.9% of the ABC molecules were recognized by C1.

This experiment demonstrates that the current state-of-the-art dextran chip does not provide the sensitivity necessary for determination of biological binding between ABC and C1.

EXAMPLE 9

SPR Determination of Monoclonal Antibodies Using Chip Derivatized with Self-Assembled Monolayer of Alkyl Thiol Terminating in Metal Chelate Coordinated by Polyamino Acid-Tagged T Cell Receptor As in examples 5 and 7, this example demonstrates the sensitivity of the SPR technique using a chip derivatized in accordance with the present invention. An SPR chip prepared in accordance with example 2 was mounted in the SPR instrument described above, modification of the chip to chelate nickel dication was effected in accordance with example 3, the modified chip surface was exposed to ABC (example 8) including a histidine tag at the constant domain, and SPR response to introduction to the chip surface of C1 and βF1 was investigated.

Figure 4:
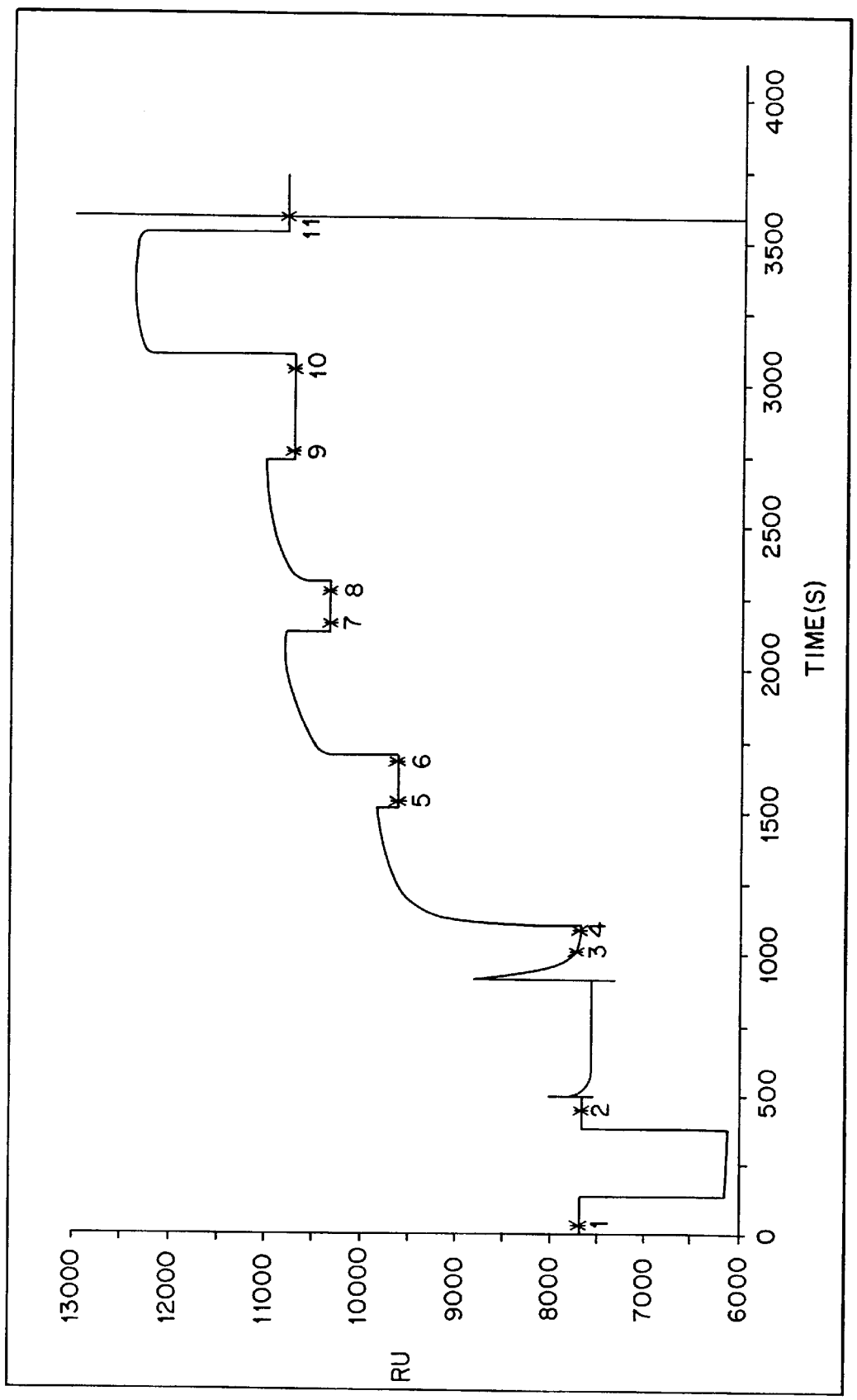
FIG. 4 is a SPR sensorgram illustrating response of a chip, derivatized in accordance with the present invention and carrying a T cell receptor (ABC), to monoclonal antibodies C1 and BF1.

FIG. 4 illustrates a sensorgram plotting resonance units as a function of time associated with this example. The flow rate of sample across the chip surface was 5 ul/min. The sensorgram of FIG. 4 is labeled with reference numerals that correspond to the steps of the experimental protocol below.

1. (t=42 s) chip description
2. (t=448 s) end of injection of 1 mM NAOH
3. (t=1017 s) end of injection of 1% $NiSO_4$
4. (t=1097 s) preinjection baseline
5. (t=1553 s) end of injection of ABC at 0.125 mg/ml; solution contains 0.02M imidazole
6. (t=1696 s) preinjection baseline
7. (t=2177 s) end of injection of C1 at 0.2 mg/ml; solution contains 0.02M imidazole
8. (t=2288 s) preinjection baseline
9. (t=2781 s) end of injection of βF1 at 0.2 mg/ml; solution contains 0.02M imidazole
10. (t=3075 s) preinjection baseline
11. (t=3604 s) end of injection of myc-a at 0.2 mg/ml; solution contains 0.02M imidazole Tabulated below are protein absorption response values (AbsResp; RU units) and response values relative to preceding baseline (RelResp; RU units) corresponding to the protocol steps above.

|     | Time    | AbsResp | RelResp |
|-----|---------|---------|---------|
| 1.  | 42.00   | 7671    |         |
| 2.  | 448.50  | 7660    |         |
| 3.  | 1017.50 | 7730    |         |
| 4.  | 1097.00 | 7695    |         |
| 5.  | 1553.50 | 9640    | 1945    |
| 6.  | 1696.00 | 9634    | 1939    |
| 7.  | 2177.00 | 10376   | 742     |
| 8.  | 2288.00 | 10353   | 719     |
| 9.  | 2781.00 | 10761   | 408     |
| 10. | 3075.00 | 10739   | 386     |
| 11. | 3604.00 | 10830   | 91      |

1,945 RU's of ABC bound to the Ni surface. The interaction with C1 led to an absorption increase of 719 RU's, while that with βF1 led to an additional 386 RU's. Finally, the myc-a antibody binding led to a 91 RU increase. The ratio of C1:ABC was 1:2.7. The ratio of C1:βF1 was 1.9:1. Since the molecular weight of C1 is 3.7 times that of ABC, the molar ratio of C1:ABC is 1:10, which implies that 10% of the ABC molecules were recognized by C1. In separate in vivo inhibition assays, we consistently found that 10% of the ABC was correctly folded, We therefore conclude that in this example 100% of the correctly folded ABC was oriented on the gold chip with the C1 binding site in the accessible "up" position with respect to the chip surface. This is in contrast to 9% retained activity in example 8.

This example demonstrates that essentially all of the binding partners immobilized at the chip surface in accordance with the present invention were oriented so as to expose in a direction away from the chip surface the recognition region of the binding partner for the biological molecule sought to be captured.

EXAMPLE 10

Fabrication of Chip Derivatized with Self-Assembled Monolaver of Alkyl Thiol Terminating in Biological Binding Partner of DNA, to Expose DNA For Binding Studies This prophetic example describes preparation of an alkyl thiol terminating at its exposed end in a nucleic acid sequence, and a surface derivatized to carry a self-assembled monolayer including such species. Specifically, an SPR chip is primed to receive underderivatized dsDNA, provided by the user, which has been modified by the generation of an EcoR I site at one end.

A protected, single-stranded oligo is prepared via standard methods, as described in the Gene Assembler manual, Pharmacia Biosensor. The oligo is at least 25 base pairs long, and is a mixed, nonself-complementary sequence, terminated with a dG at the 3' end. The polymer-supported oligo is dried under vacuum overnight.

The 5' dimethoxytrityl (DMT) protecting group is deprotected at pH 3.0 in water for 10 minutes at room temperature. The reaction is stopped by freezing on dry ice, and the residue is filtered. See Ferentz, A.; Keating, T. A.; Verdine, G. L. J. Am. Chem. Soc. 115, 9006–9014 (1993).

From 11-mercaptoundec-1yl oligo(ethyleneglycol) (6; see example 2) is synthesized the S-DMT-protected derivative. See Zervas, L. L.; Photaki, I. J Am. Chem. Soc. 84, 3887–3891 (1962). The 5' hydroxyl of the oligo is activated with carbonyl diimidazole. See Wachter, I.; Jabloski, J. A; Ramachandran, K. L. Nucleic Acids. Res. 14, 7985–7994 (1986).

The protected alkyl thiol is added to the activated oligo in dioxane water for 30 minutes at room temperature. Excess reagent is washed away with dry dioxane, followed by methanol, and the product is dried in a desiccator overnight. The remaining protecting groups and the solid support are deprotected by treating with 25% aqueous ammonia for 6 hours at 60° C. The aqueous ammonia is chilled at 0° for 30 minutes, the polymer support is filtered, and the ammonia evaporated.

The derivatized oligo is purified via 8% PAGE-7M urea, then via G-10 Sephadex chromatography. The oligo is reduced with silver nitrate/DTT and rechromatographed. See Connolly, B. A.; Rider, P. Nucleic Acids Res. 12, 4485–4502 (1985).

An oligo of sequence complementary to that made in step 1, with an additional 4 bp's at the 5' end (3'-TTAA-5') is purchased. The purified, derivatized oligo from the previous step is hybridized with the complementary oligo by denaturation at 75° C., and annealed at 55° C. This yields an alkyl thiol attached to a dsDNA, which is terminated with an EcoR I restriction nzyme site. EcoR I is widely available commercially, for example from New England Biolabs.

This DNA ligand is mixed with a self-assembled monolayer-forming, nonspecific binding-inhibiting species, specifically, 11-mercaptoundec-1yl oligo(ethyleneglycol) (6; see example 2) in a 5:95 molar ratio, respectively. The chip surface is prepared as described in example 2. This completes the preparation of a commercial chip.

EXAMPLE 11

Modification of Chip Derivatized with Self-Assembled Monolayer of Alkyl Thiol Terminating in Biological Binding Partner of DNA, to Expose DNA for Binding Studies In this prophetic example, selected dsDNA that the user wishes to present on the chip surface is cut, via standard methods, with EcoR I. The cut DNA is ligated to the DNA already on the chip using DNA ligase (New England Biolabs). The chip is now ready for use in a biosensor.

Advantages of the chip prepared in accordance with examples 10 and 11 follow. The current state-of-the-art chip, available from Pharmacia Biosensor for use in the BIAcore™ SPR instrument, presents a dextran surface to which strepavidin is attached. The user must either derivative the desired DNA with biofin, or purchase biotinylated DNA. In the former case, the reaction is difficult and biotinylation may occur at any number of sites, leading to a lack of control over orientation on the chip. Furthermore, biotinylation may block an interaction site on the DNA. Commercially available biotinylated DNA is very expensive and cannot be obtained in lengths much greater than 70 base pairs. The derivatized DNA then is attached to the chip surface via interaction between the biotin and the strepavidin.

Another disadvantage of the prior art strepavidinibiotin technique includes the fact that many of the compounds which bind negatively charged DNA are positively charged. Since the dextran surface retains a number of negatively charged carboxylates, interactions of an electrostatic nature may be mistaken for binding with the target DNA. Also, kinetic analyses of binding would be compromised due to the additional attractive force created by the negative carboxylates. Still another disadvantage of the prior art technique is that the strepavidin on the chip surface gives rise to nonspecific interactions with many target compounds.

The procedure described in this example for the preparation of the DNA chip may be applied to the preparation of an analogous RNA chip.

EXAMPLE 12

Fabrication and Modification of Chip Derivatized with Self-Assembled Monolayer of Alkyl Thiol Terminating in Biological Binding Partner of DNA, to Expose DNA for Binding Studies This example describes preparation of a SAM terminating at its exposed end in a nucleic acid sequence, and a surface derivatized to carry a self-assembled monolayer including this species in combination with a background layer of inert SAM-forming species. In particular, a SAM presenting short strands of single-stranded DNA (ssDNA; 34, with reference to FIGS. 8–10) above a background layer of inert non-binding thiols 30 was prepared, followed by hybridization of double-stranded DNA containing specific protein binding sites to the chip surface, the double-stranded DNA having a single stranded tail complementary to that presented by the chip. Specifically, an SPR chip was primed to receive underderivatized dsDNA modified by the generation of an EcoR I site at one end.

An SAM-forming nucleic acid species 34 was synthesized as follows. Species (1) was reacted with tosyl chloride in pyridine at room temperature for 4–6 hours to give species (8):

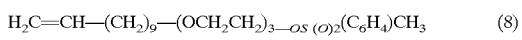

This was reacted with $NaN_3$ in N,N-dimethylformamide at 60° C. for approximately 4–8 hours giving species (9):

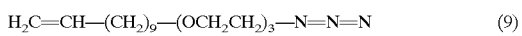

Species (9) was reacted according to one of two methods. In the first method, species (9) was reacted with $PPh_3$ in TBF followed by reaction with water. In a preferred method, reaction took place with $LiAlH_4$, refluxing for two hours in THF, followed by reaction with water. In either case species (10) was recovered:

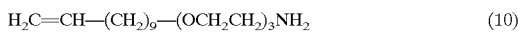

Species (10) was reacted with $(CH_3)_3C$—O—C(O)—O—C(O)O—$C(CH_3)_3$ and $Et_3N$ in DMF for 0.5 hours at 50° C. giving species (11):

H₂C=CH—(CH₂)₉—(OCH₂CH₂)₃N(H)C(O)—O—C(CH₃)₃ (11)

which was reacted with six equivalents of CH₃C(O)SH and CH₃—C(CH₃)(CN)—N=N—C(CH₃)(CN)—CH₃. The reaction mixture was irradiated with a medium pressure 450 Watt lamp (Hanovia) for five hours giving species (12):

(H₃C)C(O)S(CH₂)₁₁—(OCH₂CH₂)₃N(H)C(O)—O—C(CH₃)₃ (12)

Species (12) was reacted with HCl/MeOH(0.1M) and refluxed for 4–6 hours to give species (13):

HS(CH₂)₁₁—(OCH₂CH₂)₃NH₂ (13)

which was reacted with I₂, O₂, and CH₃(CH₂)₃SH in dimethoxyethane for 4 hours to give species (14):

[S(CH₂)₁₁—(OCH₂CH₂)₃NH₂]₂ (14)

A 10-base strand of DNA was synthesized on a DNA synthesizer. While still attached to the resin, the 5'-deprotected DNA was reacted with carbonyldiimidazole (CDI) to give the 5'-imidazolylacylated product. This was subsequently reacted with species (14), first in dioxane for 0.5–1 hour, then with NH₃ at 60° C. for 6–8 hours to give species (15):

[S(CH₂)₁₁—(OCH₂CH₂)₃N(H) C(O)—O—DNA—OH(3')]₂ (15)

Species (15) was removed from the resin by standard purification techniques except that NH₄OH at 65° C. for 8 hrs was used, giving (16):

[S(CH₂)₁₁—(OCH₂CH₂)₃N(H)C(O)—O—DNA]₂ (16)

The product, after removal from resin after purification (HPLC), was a thiol derivatized with single-stranded DNA. HPLC analysis showed the generation of a new species (50–75% pure) that eluted from the column upon purification much later than the underivatized 10-mer DNA and slightly slower than the 10-mer DNA with the trityl group still attached to the 5' end. The elution profile of the product is consistent with expected results for DNA derivatized with the alkyl thiol chain.

Species (16) formed pairs of exposed nucleic acid strands, with the -S-S-bridge in the center of the molecule adhering to the surface. Species (16) is represented as species 34 in the figures.

The selected dsDNA desirably immobilized at the surface was then cut, via standard methods, with EcoR I. The cut DNA was ligated to the DNA already on the chip using DNA ligase, resulting in a chip ready for use in a biosensor.

To form a self-assembled monolayer, SAM-forming ssDNA species (16; 34 in the figures) was mixed with the inert, non-binding ethyleneglycol-terminated thiol (6; 30 in the figures) in mM ethanol solution in a molar percent of inert species of about 0.5–3%. A gold 26-coated glass substrate 22 then was incubated in this solution. A SAM 28 was formed on the gold surface 24. It was assumed that any DNA not derivatized with thiol did not bind the gold surface. Additionally, any amino-thiol that did not react with the 5' hydroxyl of the DNA would have been lost during the extensive washing steps while the DNA was still resin-bound. Therefore, DNA-SAMs were formed without further purification. Good SAM formation from acetonitrile was significantly more effective than from ethanol, forming (per SPR analysis) ordered SAM arrays when the gold substrate was incubated at 45° C. for 12 hours. The surfaces were well behaved in that they resisted the binding of proteins and (as FIGS. 5–7 and related discussion show) these surfaces hybridized DNA if and only if the DNA had a single stranded tail of exactly complementary sequence to that presented by the chip.

Once dsDNA 36 was hybridized to the covalently-immobilized single-stranded DNA 34 at the surface, the nick 40 in the coding strand was covalently joined by DNA ligase but only in cases in which the 5' hydroxyl of the incoming oligo was phosphorylated. It was observed that performing a DNA ligation reaction resulted in more DNA stably bound to the surface but only if the 5' hydroxyl was first phosphorylated. When DNA containing Gal4 recognition 10 sites was hybridized to the DNA-SAM, it selectively bound Gal4 protein but not another DNA-binding protein Lex-B17. Our results indicate that we have generated a DNA-presenting SAM.

EXAMPLE 13

Characterization of Chip Derivatized with Self-Assembled Monolayer of Alkyl Thiol Terminating in Biological Binding Partner of DNA Varying amounts of the ssDNA-derivatized disulfide (16) were mixed with the inert, triethylene glycol terminated thiol (6) which defined the major component (1 mM) in acetonitrile solutions. Pre-cleaned (H₂SO₄/H₂O), gold-coated glass slides were incubated at 45° C. for 8–12 h in the solutions. The slides were cut and mounted on plastic CM-5 SPR chip cassettes (Pharmacia). The experimental chips were docked in a BIACore™ SPR instrument and experiments were performed to assay the ability of the chip to hybridize single-stranded DNA (ssDNA) complementary to the strand of the DNA-derivatized thiol.

Three DNA samples were sequentially injected over the same flow cell of a chip. The samples contained double-stranded DNA (dsDNA) containing 2 Gal4 protein binding sites and the three DNA samples included: 1) DNA without a single-stranded tail, 2) DNA with a 10-base single stranded tail whose sequence content was complementary to strand 34 presented by the chip, but having a scrambled sequence and 3) DNA with a 10-base single stranded tail exactly complementary to that presented by the chip. 35 μL of each DNA sample (DNA concentration=[14 pM/μL] in 400 mM NaCl) as separately injected over the DNA-SAM. Experiments were run at RT at a constant flow rate of 5 μL/min in PBS (137 mM NaCl). As discussed above, the binding of molecules to a chip surface is detected as a net increase in resonance units (RUs). A net change in RUs resulted only after the injection of sample (3), that is, the DNA bearing a single-stranded tail whose sequence was exactly complementary to strand 34 of the DNA-thiol SAM immobilized on the chip.

Figure 5:
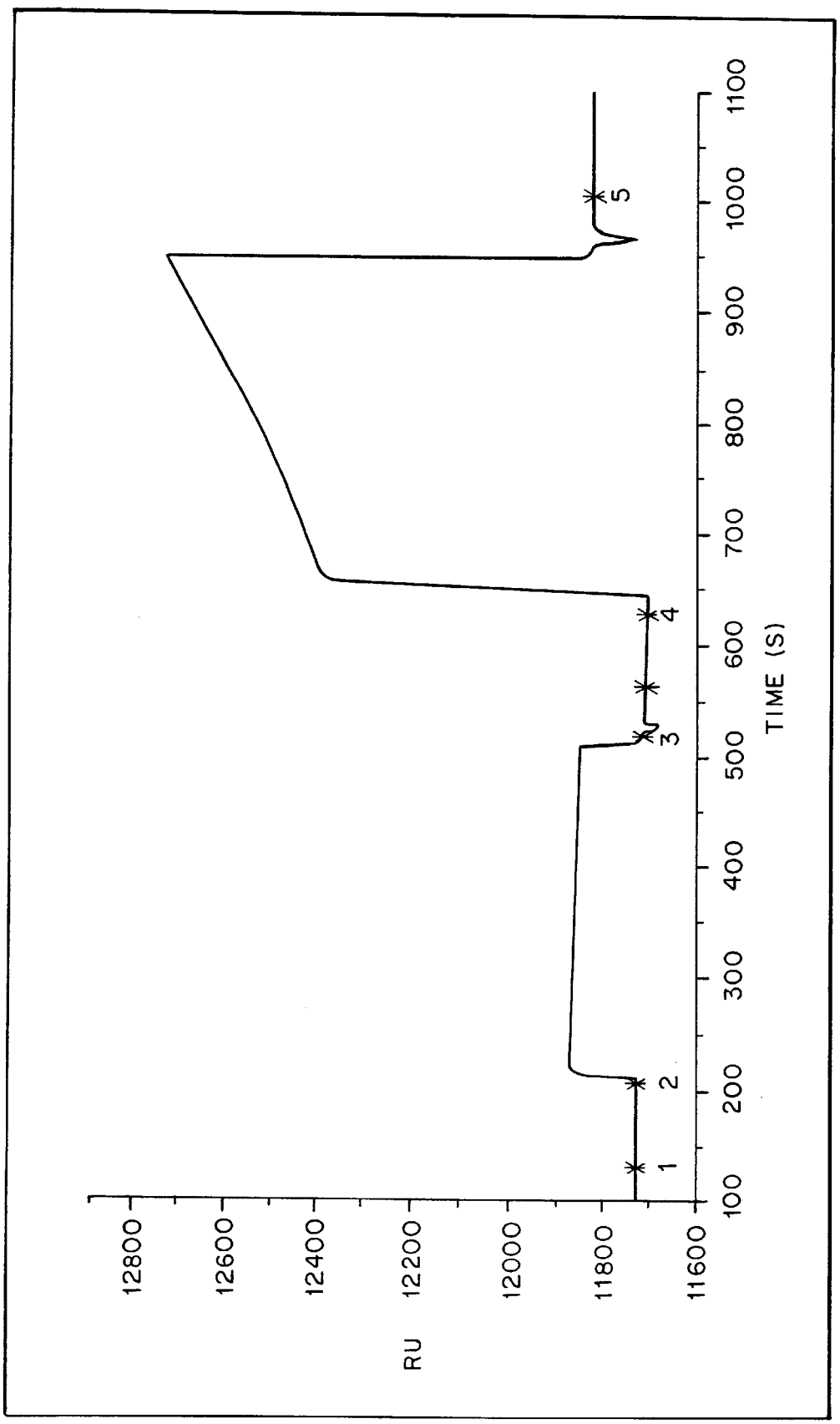
FIG. 5 is a SPR sensorgram illustrating response of a chip, derivatized in accordance with the invention to present a single-stranded nucleotide sequence, first to double-stranded DNA carrying a single-stranded "tail" scrambled with respect to that presented by the chip, and then to a single-stranded "tail" complementary to that presented by the chip.

FIG. 5 illustrates a sensorgram plotting RU as a function of time associated with the experiments involving DNA with a single-stranded scrambled tail and DNA with a 10-base single stranded tail complementary to nucleic acid strand 34 presented by the chip. The sensorgram of FIG. 5 is labeled with reference numerals that correspond to the steps of the experimental protocol below.

1. (t=130 sec) end of injection of 137 mM NaCl buffer.
2. (t=205 sec) preinjection baseline.
3. (t=519 sec) end of injection of DNA with 10-base single-stranded scrambled "tail".
4. (t=624 sec) preinjection baseline.
5. (t=1003 sec) end of injection of DNA with 10-base single-stranded tail complementary to that presented by the chip.

Tabulated below are DNA absorption response values (AbsResp; RU units) and response values relative to preceding baseline (RelResp; RU units) corresponding to the protocol steps above.

|   | Time    | AbsResp | RelResp |
|---|---------|---------|---------|
| 1.| 130.50  | 11726   | −4      |
| 2.| 206.50  | 11722   | −7      |
| 3.| 519.50  | 11719   | −3      |
| 4.| 624.50  | 11710   | −8      |
| 5.| 1003.00 | 11822   | 112     |

Figure 6:
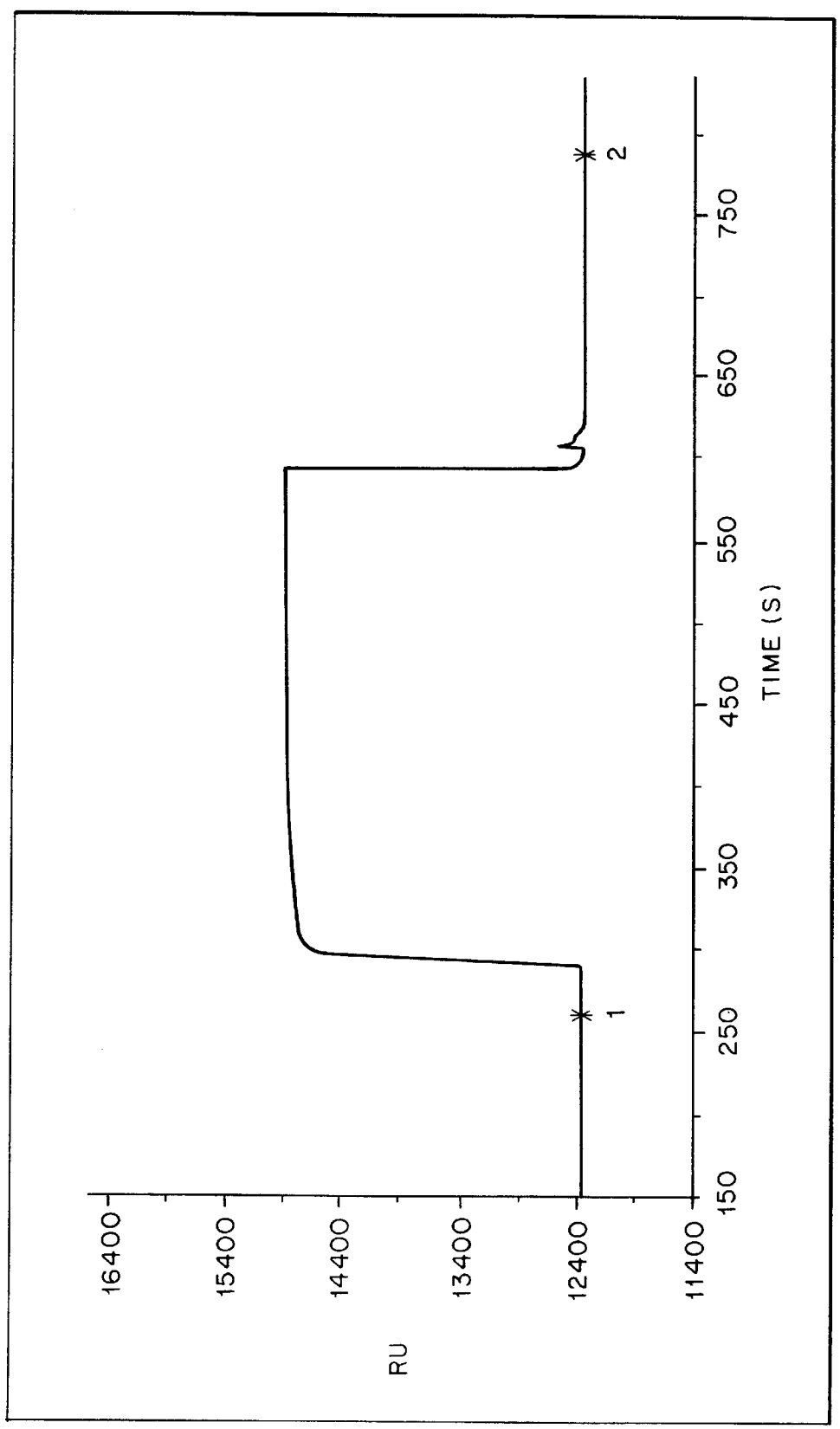
FIG. 6 is a SPR sensorgram illustrating response of the chip of FIG. 5 to double-stranded DNA without a "tail"

FIG. 6 is a sensorgram plotting RU as a function of time associated with injection of DNA without a single-stranded tail. The sensorgram of FIG. 6 is labeled with reference numerals that correspond to the steps of the experimental protocol below.

1. (t=259 sec) chip description
2. (t=787 sec) end of injection of DNA without tail Tabulated below are DNA absorption response values and response values relative to preceding baseline corresponding to the protocol steps above.

|   | Time   | AbsResp | RelResp |
|---|--------|---------|---------|
| 1.| 259.00 | 12380   | 0       |
| 2.| 787.00 | 12383   | 2       |

This experiment demonstrates that a biosensor surface prepared in accordance with the invention provides a nucleotide sequence oriented to expose away from the chip surface the nucleotide 34 for binding to a complementary nucleotide.

We found that the DNA hybridized to the chip was more stably bound if it was enzymatically ligated to the DNA presented by the chip. To do this, the chips were docked in the BIAcore™ SPR instrument and equilibrated in PBS. Baseline measurements were recorded for each flow cell. The chips were then removed from the instrument and were bathed in 100 μL of a solution containing DNA with a 10-base single-stranded tail complementary to strand 34 presented by the chip for 0.5 h at RT. The excess solution was removed from the chip surface and 200 μL of DNA ligase in ligase buffer was added to mend nick 40 in the strand. The stability of the bound DNA increased if and only if DNA ligase was present and the 5' end of the incoming synthetic DNA strand was phosphorylated. These results reflect the advantage of using DNA ligase to join two DNA strands through a 5' phosphate group.

EXAMPLE 14

SPR Determination of Specific Protein Binding to DNA Chip

Figure 7:
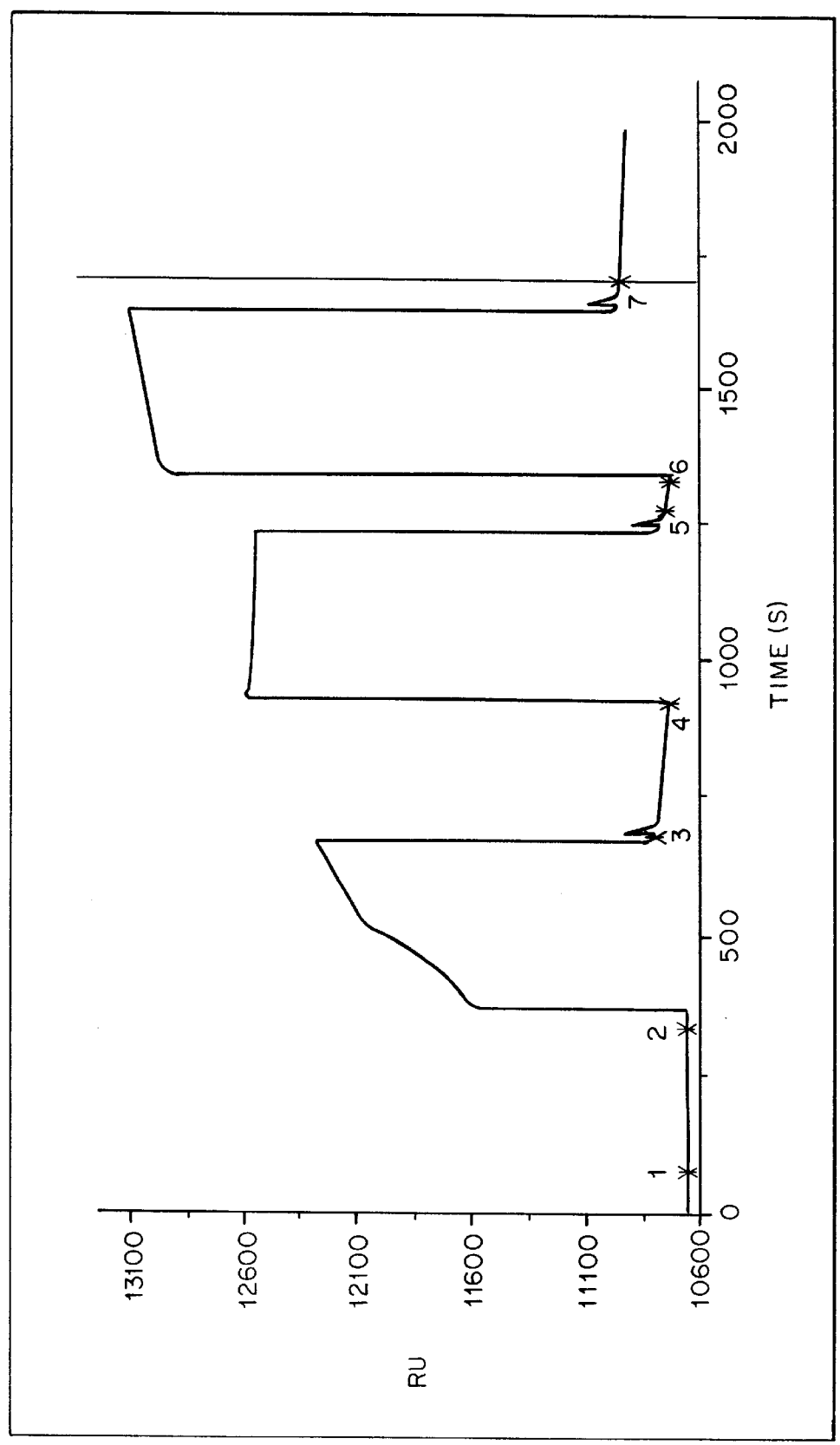
FIG. 7 is a SPR sensorgram illustrating response of a chip carrying double-stranded DNA including 2Gal4 binding sites to Gal4 and to LexB17.

Experiments were performed to determine whether these chips as described in Example 13 could specifically bind proteins to binding sites on the hybridized DNA while resisting the non-specific adsorption of irrelevant proteins. In particular, SPR experiments were conducted to investigate the binding of Gal4(1–100) as opposed to Lex-B17 on chips carrying hybridized DNA bearing 2Gal4 protein binding sites. FIG. 7 is a sensorgram plotting resonance unit as a function of time associated with this example. The sensorgram of FIG. 7 is labled with reference numerals that correspond to the steps of the experimental protocol below.

1. (t=77 sec) chip description
2. (t=335 sec) end of injection of 137 mM NaCl
3. (t=677 sec) end of injection of DNA including 10-base pair complementary to that presented by the chip
4. (t=923 sec) preinjection baseline
5. (t=1275 sec) end of injection of Lex-B17 (0.125 mg/ml)
6. (t=1327 sec) preinjection baseline
7. (t=1700 sec) end of injection of Gal4 (0.125 mg/ml)

Tabulated below are protein absorption response values and response values relative to preceding baseline corresponding to the protocol steps above.

|   | Time    | AbsResp | RelResp |
|---|---------|---------|---------|
| 1.| 77.50   | 10651   | 0       |
| 2.| 335.50  | 10658   | 7       |
| 3.| 677.50  | 10791   | 133     |
| 4.| 923.00  | 10732   | −59     |
| 5.| 1275.50 | 10762   | 29      |
| 6.| 1327.50 | 10741   | −20     |
| 7.| 1700.00 | 10955   | 213     |

Experiments were performed also to determine whether the concentration of the SAM-forming nucleotide on the chip had an effect on protein binding. Table 1 shows a comparison of four different chips with different DNA concentration at the chip surface, the DNA including 2 Gal4 protein binding sites.

TABLE 1

| dsDNA CONTAINING 2 GAL4 BINDING SITES (Δ RUs) | GAL4 BOUND (RUs) | LEX B17 BOUND (RUs) |
|---|---|---|
| 52   | 164  | —  |
| 74   | 213  | 0  |
| 441  | 365  | —  |
| 1378 | 1079 | 96 |

SPR experiments showed that hybridized DNA bearing 2 Gal4 protein binding sites preferentially bound Gal4 (1–100) protein over Lex-B17. Additionally, there appears to be a direct correlation between the amount of DNA hybridized to the chip and the amount of Gal4 that subsequently bound to it.

The observed preference of chip-hybridized DNA containing Gal4 binding sites for Gal4 protein over Lex-B17 was reversed when DNA bearing Lex binding sites was hybridized to the chip surface (see Table 2). DNA containing 2 Lex binding sites and a single-stranded complementary tail was annealed, then ligated to a ssDNA chip. The chip was then docked in a BIAcore™ SPR instrument and equimolar concentrations of either Lex-B17 or Gal4 were separately passed over three flow cells of the same chip.

TABLE 2

| FLOW CELL | GAL4 BOUND (RUs) | LEX B17 BOUND (RUs) |
|---|---|---|
| 1 | —   | 363 |
| 2 | 136 | —   |
| 3 | —   | 345 |

EXAMPLE 15

Detection of Small-Molecule Interactions Based on Electron Transfer

This prophetic example describes biospecific SAMs (S—R—ch or X—R—NA SAMs) that are part of a biosensor for the detection of protein-protein, protein-small molecule, protein-DNA, or DNA-DNA (hybridization) interactions based on electron transfer. A biosensor for detecting DNA-DNA interactions is described first, with reference to the figures. A SAM comprised of DNA-thiol 34 (described in Examples 12 and 13) as the minor component and a tri-ethyleneglycol terminated alkane thiol ((6); 30 in the figures) as the major component in a ratio of about 3:97 is formed on a gold-coated electrode. With reference to FIG. 9, double stranded DNA (dsDNA) 36 having a single stranded tail 38, complementary to that of the DNA-thiol 34, is hybridized to the DNA-SAM on the electrode. The nick 40 between the 3' end of DNA-thiol 34 and the 5' end of incoming dsDNA 36 is covalently mended with the enzyme DNA ligase. The result is that the DNA of the DNA-SAM has been covalently extended with DNA of interest (dsDNA 42). Incoming dsDNA 42 contains a polylinker (a stretch of DNA containing recognition sequences at which specific restriction enzymes cleave dsDNA) so that it can be cut with restriction enzyme 46, and then *E. coli* produced DNA 50 (FIG. 10), cut with enzyme 46, is ligated onto the SAM to form surface-immobilized dsDNA 52. The nick in the coding strand optionally is mended. Since only the sense strand 54 is covalently attached to the SAM, heat or chemical treatment will dissociate the anti-sense strand 56.

After dissociation, the resultant single-stranded DNA (ssDNA 72, now with reference to FIGS. 11 and 12) then is probed, by hybridization, with specific DNA sequences 70. If specific DNA sequences 70 are the complement of sequences 72, then hybridization will occur and a flow of current will be measured at ammeter 74 that is distinguishable from situations in which hybridization does not occur.

Referring now to FIG. 13, where different ssDNA strands are provided in each of the different isolated regions 84, 86, 88, 100 . . . when potential difference is placed across the two electrodes, distinguishable conductance occurs only when the two DNA species hybridize to complete the circuit, thus existence of unknown samples can be determined.

The array schematically illustrated in FIG. 13 is advantageous in that either or both of the SAMs on electrodes 62 or 66 can be reused. For example, a series of different species provided on electrode 66 can be used repeatedly with a series of different electrodes 62 each including a single, but different species across the entire electrode. Similarly, a single electrode 62 can be used with a variety of different arrays on different electrodes 66.

This assay is usefull in sequencing the human genome. To determine what DNA sequence abuts the last sequence mapped, random sequences of DNA from a certain chromosome are obtained by standard PCR techniques. By using PCR primers that contain the recognition sequence of a particular restriction enzyme, all the DNA samples, generated from the parent DNA, have identical flanking restriction enzyme sites. As a heterologous species, they are ligated into a bacterial expression vector which is used to transform *E.coli* cells. Bacterial colonies, each expressing a single DNA species, are picked and the plasmid DNA is extracted. Of the hundreds of thousands of DNA species, only oligos that also contain part of the previously-identified abutting sequence need to be identified. The anti-sense strand first is "probed" or the abutting sequence hybridized to the unknown DNA oligos and then only the oligos that hybridize to the probe need to be sequenced. Each *E. coli* derived DNA species actually must be separately immobilized to facilitate characterization once an interaction has been detected. This is accomplished when arrays of micro-electrodes or AFM tips, each carrying a single DNA species, interfaces with arrays of probe-bearing micro-electrodes. Photo-resist methods or other methods described above are employed to create a uniform array of gold islands bordered by hydrophobic surfaces. The DNA-SAM is uniformly assembled over the array and polylinker attached. Attachment of multiple DNA species is carried out by laying down individual droplets of single species DNA and ligase containing solution over the spatially addressable gold islands in the array. Alternatively, a microelectrode array displaying a single species interfaces with a diverse DNA probe array synthesized by light-directed spatially addressable synthesis (Fodor, S. P. A., Read, J. L. Pirrung, M. C., Stryer, L., Lu, A. T., Solas, D., "Light-Directed, Spatially Addressable Parallel Chemical Synthesis", *Science*, 251 (1991) pp. 767–773). Thus a generic DNA-SAM is used to present specific oligos of any length or sequence for interaction studies with other molecules. Similar strategies enable the detection of protein-peptide interactions by immobilizing histidine-tagged proteins to one array of NTA-SAM derivatized microelectrodes and interfacing it with spatially addressable peptides immobilized on a second array.

EXAMPLE 16

DNA Computer

In this prophetic example, a DNA computer is made (Adleman, L. M., "Molecular Computation of Solutions to Combinatorial Problems", *Science*, 266 (1994) pp. 1021). The four bases that make up DNA are used to code information sequentially along the molecule. Like the binary code in electronic computers, it can be used to define problems, perform sequential processing (a program) and read out solutions. DNA computing requires that random DNA (all possible solutions) be probed with short oligos (certain criteria that must be met). The solution is the sequence of the random DNA that satisfies all the criteria. To solve the problem of how to identify which of the random oligos satisfies all the criteria (exactly hybridized to all the probe oligos), a DNA-SAM derivatized with random ssDNA is probed with an array of probe (starting point) DNA. Specific oligos that code for certain criteria are added into the solution. The addition of DNA ligase makes the sequence of the "solution" strand permanent. Which probe now carries the exact sequence is detected making use of the time dependence of electron transfer through double stranded DNA compared with transfer through single stranded DNA, as described above. The probe sequence that is shown to carry the solution is ascertained by PCRing the species of that single probe.

EXAMPLE 17

Electronic-Property Determination of Disease State Involving Mis-Folded Protein This prophetic example describes a simple technique for determining a disease state involving mis-folded protein in an early stage of the disease.

With reference to FIG. 16, a system 120 is provided in which normal peptides are presented by SAM 124. The normal peptide is directly attached to a thiol and then the derivatized species used to form a mixed SAM (with NSB-resistant species 30) or the peptide is attached to a metal elate via polyamino acid tag. In a particularly sensitive arrangement, the peptide is attached to the surface of electrode 122 via a "Molecular Wire" (*Science*, 271, 1705–1707, 1996, incorporated herein by reference).

Fluid or tissue extracts from a mammal suspected to be infected with the mis-folded protein disease state such as TSE are injected into inlet 93 of container 94. Where prions are present, they cause a conformational change in the surface-immobilized normal protein, which changes the electronic properties of the capacitor system, as detected at impedance sensor 99.

The normal protein need not be immobilized at the surface but may be free in the capacitor medium.

The medium of the system may contain other elements such as catalysts, sugars, lipids, sulfated glycosaminoglycans or solvents to hasten fibril and plaque formation which occurs in the diseased state. It may also contain normal protein to amplify the detection of the disease state when prion is present the added normal protein will become mis-folded and, in turn, cause the surface-immobilized protein to become mis-folded. Other physical parameters of the systems, such as temperature, pressure, electrical or magnetic field densities can be optimized to favor more rapid progression of conformational changes. For example, the system can be pulsed with various frequencies of electromagnetic radiation (e.g., Ghz range) for this purpose.

The advantages of the system over prior art antibody staining of infected tissue sections include the following. infectious samples are in solution and not dependent upon a level of prion aggregation before being detectable and so earlier detection of infection is possible. The method of detection does not depend upon the viability of other less robust proteins such as antibodies, therefore the system can be subjected to harsh physical or chemical conditions (organic solvents such as toluene, THF, ACN, phenol and the like, and pH outside of the physiological range of 6.8–8.2) or frequencies which can promote the conformational changes that characterize the disease. The system of the invention can be a more sensitive assay because single molecule conformational changes are detected. When MHZ frequencies are used in the detection, a 1% change in the conformation of the sample volume can be detected (six significant figures). Greater variety of samples and smaller sample sizes (needle biopsies, blood, saliva, urine, cerebrospinal or ocular fluid, lymphoid tissues, etc.) can be used. The method is specific because it measures the very change that determines the disease state, that is, the conformational change. The method is inexpensive and easily scalable, lending itself to mass screenings. The variety of sample types compatible with the method of detection makes the system applicable to the detection of prions in live animals, food products derived from animals, and animal feed. This allows of prevention of the spread of disease at several stages. Interpretation of test results does not require a high level of skill so unskilled personnel can administer the test.

Those skilled in the art would readily appreciate that all parameters listed herein are meant to be exemplary and actual parameters will depend upon the specific application for which the methods and apparatus of the present invention are being used. It is, therefore, to be understood that the foregoing embodiments are presented by way of example only and that, within the scope of the appended claims and equivalents thereto, the invention may be practiced otherwise than as specifically described.

What is claimed is:

1. A method for detecting the formation of a biological binding complex between a first biological species and a second biological species comprising:
    a) providing said first biological species immobilized on a first metal surface of an article via a self-assembled monolayer:
    b) providing said second biological species immobilized on a second metal surface of an article via a self-assembled monolayer, wherein said first and second surfaces are different;
    c) detecting electron transfer associated with the passing of an electron from the first surface to the second surface as a result of the formation of said binding complex.

2. A method according to claim 1 wherein said first and said second biological species comprise a biological binding pair.

3. A method according to claim 2 wherein said first and said second biological species are nucleic acids.

4. A method according to claim 3 wherein said first biological species is a first nucleic acid strand and said second biological species is a second nucleic acid strand complementary to said first nucleic acid.

5. A method according to claim 1 wherein said monolayer on said first surface comprises a second self-assembled monolayer forming species.

6. A method according to claim 1 wherein said monolayer on said second surface comprises a second self-assembled monolayer forming species.

7. A method according to claim 1 wherein said first and said second surfaces are electrodes.

8. A method according to claim 7 wherein said electrodes are gold.

9. A method according to claim 1 wherein said self-assembled monolayer-forming species comprise thiols.

10. A method according to claim 1 wherein said first surface is a first article and said second surface is on a second article.

11. A method according to claim 1 wherein said first and said second surfaces are on the same article.

12. A method according to claim 11 wherein said article comprises a plurality of surface, each with a different biological species.

* * * * *